(12) United States Patent
Okawa

(10) Patent No.: US 7,027,932 B2
(45) Date of Patent: Apr. 11, 2006

(54) BIOCHEMICAL EXAMINATION METHOD

(75) Inventor: Kaneyasu Okawa, Tsukui-gun (JP)

(73) Assignee: Olympus Optical Co., Ltd., Tokyo (JP)

( * ) Notice: Subject to any disclaimer, the term of this patent is extended or adjusted under 35 U.S.C. 154(b) by 31 days.

(21) Appl. No.: 10/098,822

(22) Filed: Mar. 15, 2002

(65) Prior Publication Data

US 2002/0168665 A1 Nov. 14, 2002

(30) Foreign Application Priority Data

Mar. 21, 2001 (JP) ............................ 2001-081633

(51) Int. Cl.
*G01N 33/48* (2006.01)
(52) U.S. Cl. .......................... 702/19; 702/22
(58) Field of Classification Search ................ 702/28, 702/127, 19, 20, 22; 435/287.1; 382/16; 250/562

See application file for complete search history.

(56) References Cited

U.S. PATENT DOCUMENTS 6,591,196 B1 * 7/2003 Yakhini et al. ............... 702/28

FOREIGN PATENT DOCUMENTS

| JP | 5-284998 A | 11/1993 |
|---|---|---|
| JP | 9-504864 | 5/1997 |
| JP | 2000-180922 A | 6/2000 |
| JP | 2000-338042 A | 12/2000 |
| WO | WO 93/22678 A3 | 11/1993 |
| WO | WO 95/11755 A1 | 5/1995 |
| WO | WO 99-08233 A1 | 2/1999 |
| WO | WO 00/24940 A1 | 5/2000 |
| WO | WO 00/70088 A2 | 11/2000 |

OTHER PUBLICATIONS

Vo-Dinh, T: "Development of DNA biochip: principle and applications" Sensors and Actuators B, Elsevier Sequoia S. A. Lausanne, CH, vol. 51, No. 1-3, Aug. 31, 1998, pp. 52-59, XP004153989, ISSN: 0925-4005.
Vo-Dinh T. et al: "Nanosensors and biochips: frontiers in biomolecular diagnostics" Sensors and Actuators B, Elsevier Sequoia S.A., Lausanne, CH, vol. 74, No. 1-3, Apr. 15, 2001, pp. 2-11, SP004233650 ISSN: 0925-4005.

* cited by examiner

*Primary Examiner*—Ardin H. Marschel
*Assistant Examiner*—Jerry Lin
(74) *Attorney, Agent, or Firm*—Frishauf, Holtz, Goodman & Chick, P.C.

(57) ABSTRACT

According to the present invention, there is provided a biochemical examination method of supplying a solution of a first biochemical material into an array of which respective second biochemical materials are held, and using a marker by a luminescent molecule to detect a luminescent intensity of the luminescent molecule for each probe array element of the array with an array type detector, so that a reaction state of the first biochemical material with the second biochemical materials is examined for each probe array element, the method comprising: irradiating a reference array by which the luminescent molecule is held with an excitation lighting to photograph a reference light image; irradiating the array for biochemical examination with the same excitation lighting to photograph a sample light image; and correcting the sample light image with the reference light image.

11 Claims, 21 Drawing Sheets

BIOCHEMICAL EXAMINATION METHOD

CROSS-REFERENCE TO RELATED APPLICATIONS

This application is based upon and claims the benefit of priority from the prior Japanese Patent Application No. 2001-081633, filed Mar. 21, 2001, the entire contents of which are incorporated herein by reference.

BACKGROUND OF THE INVENTION

1. Field of the Invention

The present invention relates to a biochemical examination method for examining a state of a biochemical reaction.

2. Description of the Related Art

In recent years, for "determination of arrangement by hybridization" (SBH), several methods of an arrayed hybridization reaction have been developed. Examples include an SBH using a method of a stepwise hybridization of different oligonucleotide probes and an array of DNA samples arranged on a film in a lattice form.

Moreover, a term "genosensor" has heretofore referred to a method in which oligonucleotide is bonded as a recognition element of a target nucleic acid arrangement and a complementary arrangement on the surface of a two-dimensional array. Furthermore, a concept of genosensor includes a fine processing apparatus in which hybridization can quickly be detected and a fine electronic component is present in each test portion.

With respect to the two-dimensional array, in recent years, a flow through genosensor has been provided as follows. In the genosensor, the nucleic acid recognition element is immobilized in densely charged holes or channels arranged in a spotted form over a wafer of a solid support material. A known fine processing technique can be utilized in manufacturing glass and porous silicon of a micro channel or a nano-channel useful as the support wafer. For the flow through genosensor, various known detection methods are used which include finely processed optical and electronic engineering detection components, film, charge bonding element array, camera system and phosphorescence storage technique. The following advantages are obtained from the flow through apparatus as compared with a known plane surface design.

(1) Since a surface area enormously increases, detection sensitivity is improved.

(2) A time required for the hybridization reaction is reduced (a time required for detecting the probe with an average target molecule bonded to the surface thereof is reduced to several milliseconds from several hours), the hybridization is speeded up, and error-pairing (error-pass) identification can be made in both normal reaction and reverse reaction.

(3) Since a solution can gradually flow through the porous wafer, a dilute nucleic acid solution can be analyzed.

(4) Since a droplet of a probe solution on a plane surface exposed to the atmosphere is prevented from quickly drying, chemical bond of a probe molecule to the surface in each separate region is promoted.

The flow through apparatus having the above-described advantages will be referred to as a three-dimensional array. PCT National Publication No. 1997-504864 is cited as a prior art relating to the three-dimensional array, and FIG. 27 is used to briefly describe the constitution and action of the array.

FIG. 27 is a diagram showing a tapered sample well array constituting the three-dimensional array. In FIG. 27, a plurality of tapered holes 102 are formed in a porous glass wafer 101, and tapered wells 103 are buried in the respective holes 102. The tapered well 103 includes a channel 104 having a diameter of 0.1 to 10 μm and constituting a bonding region of a bio-molecule immobilized thereto in the bottom of the well. As shown in FIG. 27, each channel 104 has a large number of micro through holes 105. The well array is used, and detection is performed in the following steps.

(1) A solution containing 4 ml of 3-glycidoxypropyl-trimetoxysilane, 12 ml of xylene, and 0.5 ml of N,N-di-isopropyl ethyl amine (Hunig base) is passed through the holes of the wafer. Subsequently, the wafer is immersed in the solution at 80° C. for five hours, flushed with tetrahydrofuran, dried at 80° C., and thereby formed into epoxysilane-derivative glass.

(2) A plurality of oligonucleotide probes having 5'- or 3'-alkylamine (introduced during chemical synthesis) are dissolved in water at a ratio of 10 μM–50 μM, and a micro amount of the solution is pipetted in the porous glass wafer 101 (silica wafer). The wafer is reacted at 65° C. overnight, the surface of the wafer is simply flushed with water at 65° C., then with 10 mM triethylamine, and a non-reacted epoxy group is removed from the surface. Subsequently, the wafer is again flushed with water at 65° C. and air-dried, so that amine-derivative oligonucleotide is bonded to epoxysilane-derivative glass.

(3) By polymerase chain reaction in which [$^{32}$P] nucleotide is taken into a product during amplification, or 5'-labeling of the amplified product using gamma-$^{32}$P[ATP]+ polynucleotide kinase, a target DNA (analysis material) is prepared. Not-taken markers are removed by Centricon filtering. Preferably, with 5'-biotin labeling of one PCR fragment, one chain can be prepared by streptoavidin affinity chromatography. The target DNA is dissolved in a hybridization buffer solution (50 mM tris-HCl, pH 8, 2 mMEDTA, 3.3M tetramethyl ammonium chloride) having a concentration of at least 5 nM (5 fmol/μl) and a specific activity of at least 5,000 cpm/fmol. The PCR fragment having several hundreds base length is suitable for the hybridization with oligonucleotide linked to the surface having at least octameter length.

(4) The target DNA sample is passed into the porous region of a chip, and incubated at 6° C. for 5 to 15 minutes, and the hybridization is performed. Subsequently, the hybridization solution is allowed to flow through the porous chip at 18° C. similarly for 5 to 15 minutes and the chip is washed. As another method, instead of tetramethyl ammonium chloride, the buffer solution containing 1MKCL, NaCl or 5.2M betaine can be used to perform the hybridization.

(5) A CCD genosensor apparatus is used to perform detection and quantitative determination of a hybridization intensity. The CCD genosensor apparatus having high resolution and sensitivity is used, and prepared for chemical luminescent, fluorescence or radioactivity marker.

In conventional arts including the above-described prior art, when each biochemical reaction state in a probe array element is detected as luminescent intensity by the same area sensor such as CCD or a line sensor, all the probe array elements need to be uniformly irradiated. This is because a luminescent state of a luminescent molecule depends on the intensity of excitation light.

It is easily considered that the intensity of the excitation light is monitored and a detected value is corrected in a space distribution of the intensity. However, even in this case, a relation between the intensity of the excitation light and the luminescent intensity is complicated, and the relation changes with the density of the luminescent molecule, temperature, time, and the like. Therefore, there is a disadvantage that each biochemical reaction state in the probe array element cannot exactly be examined.

Moreover, a noise of excitation light or a noise by a pipetting error of the probe cannot sufficiently be removed. Furthermore, the luminescent property of the luminescent molecule is not considered, and therefore there is a disadvantage that each reaction state cannot exactly be examined.

BRIEF SUMMARY OF THE INVENTION

An object of the present invention is to provide a biochemical examination method in which each biochemical reaction state in a probe array element can exactly be examined.

According to the present invention, there is provided a biochemical examination method of supplying a solution of a first biochemical material into an array for biochemical examination on a surface of which respective second biochemical materials peculiarly reacting with the first biochemical material are held, and using a marker by a luminescent molecule excited by a light to emit the light to detect a luminescent intensity of the luminescent molecule for each probe array element of the array for biochemical examination with an array type detector, so that a reaction state of the first biochemical material with the second biochemical materials peculiarly reacting with the first biochemical material is examined for each probe array element, the method comprising: irradiating a reference array by which the luminescent molecule is held with an excitation lighting to photograph a first light image as a reference light image; irradiating the array for biochemical examination with the same excitation lighting to photograph a second light image as a sample light image; and correcting the sample light image with the reference light image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 13 to 21A and 21B are flowcharts showing an examination procedure according to the third embodiment.

DETAILED DESCRIPTION OF THE INVENTION

Embodiments of the present invention will be described hereinafter with reference to the drawings.

Figure 1:
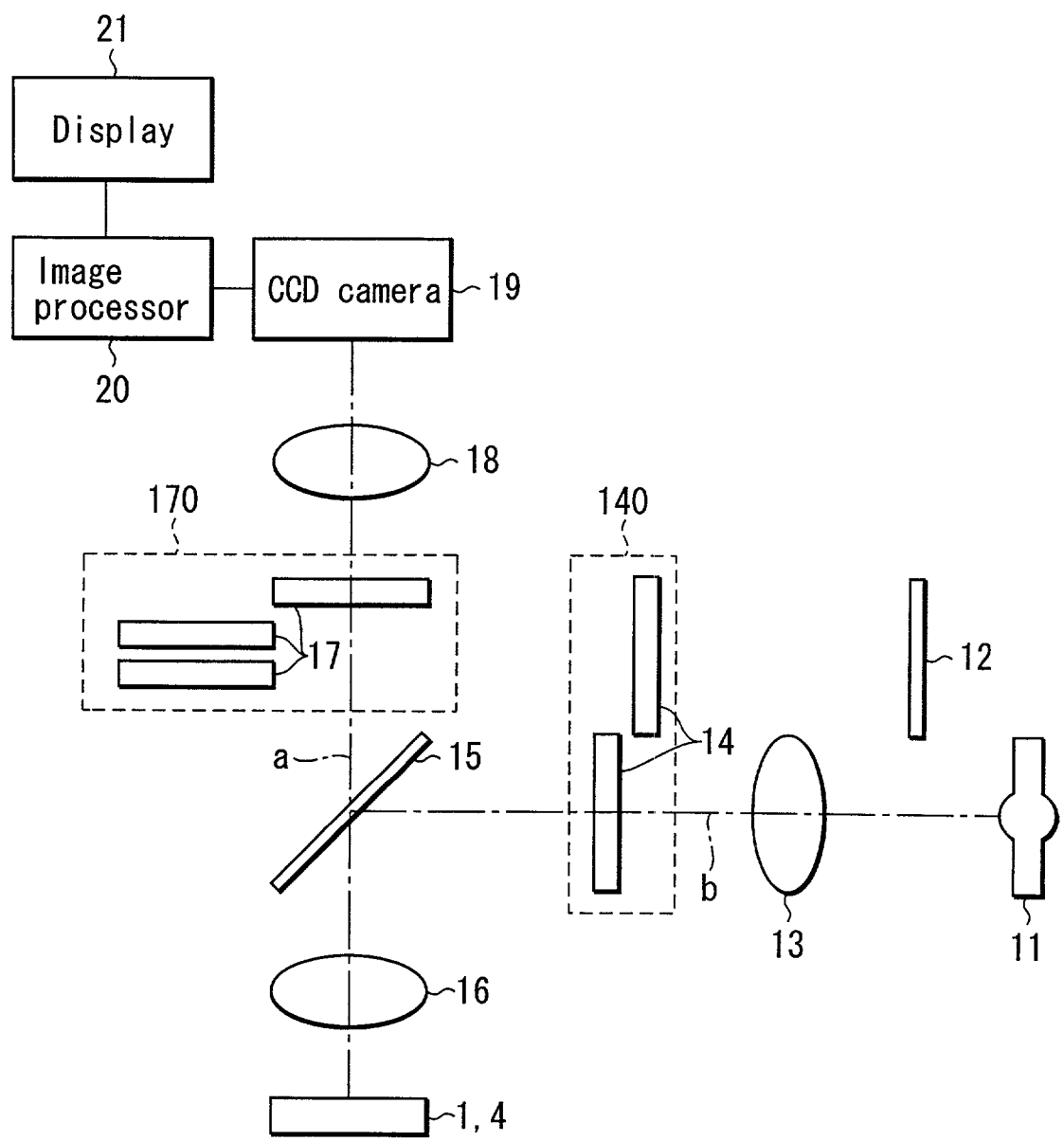
FIG. 1 is a diagram showing a configuration of a microscope apparatus for performing a biochemical examination method according to a first embodiment of the present invention.

FIG. 1 is a diagram showing a configuration of a microscope apparatus for performing a biochemical examination method according to a first embodiment of the present invention. In FIG. 1, a mercury light source or the like is used in an excitation light source 11. A shutter 12, lens 13, excitation filter unit 140 which can selectively switch two excitation filters 14, and dichroic mirror 15 are disposed on a light path of an excitation light emitted from the light source 11. An objective lens 16, and an array for biochemical examination 1 or a reference array 4 described later are disposed on a reflected light path of the dichroic mirror 15. Moreover, an ND filter unit 170 which can selectively switch a plurality of ND filters 17, image forming lens 18, and CCD camera 19 are disposed on a transmitted light path of the dichroic mirror 15. The CCD camera 19 is connected to an image processor 20, and the image processor 20 is connected to a display 21.

Figure 2A:
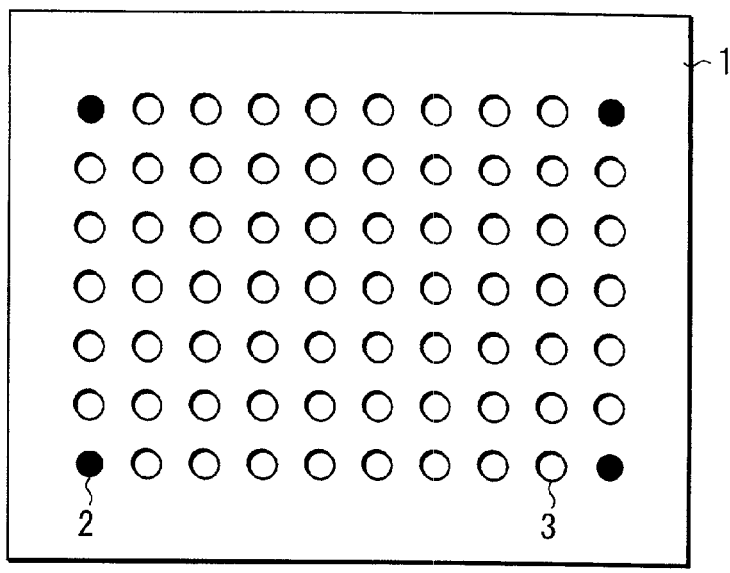
FIGS. 2A and 2B are diagrams showing a schematic configuration of an array for biochemical examination according to the first embodiment of the present invention.
Figure 2B:
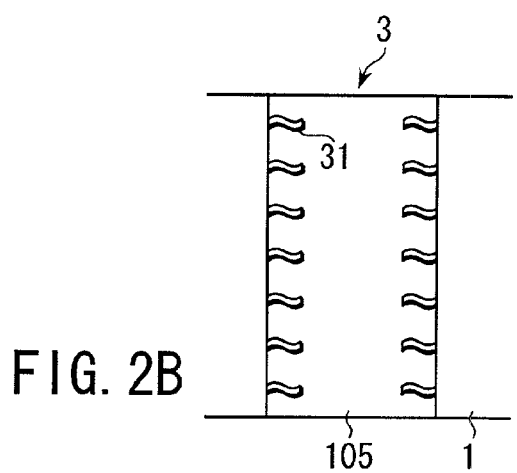
Figure 27:
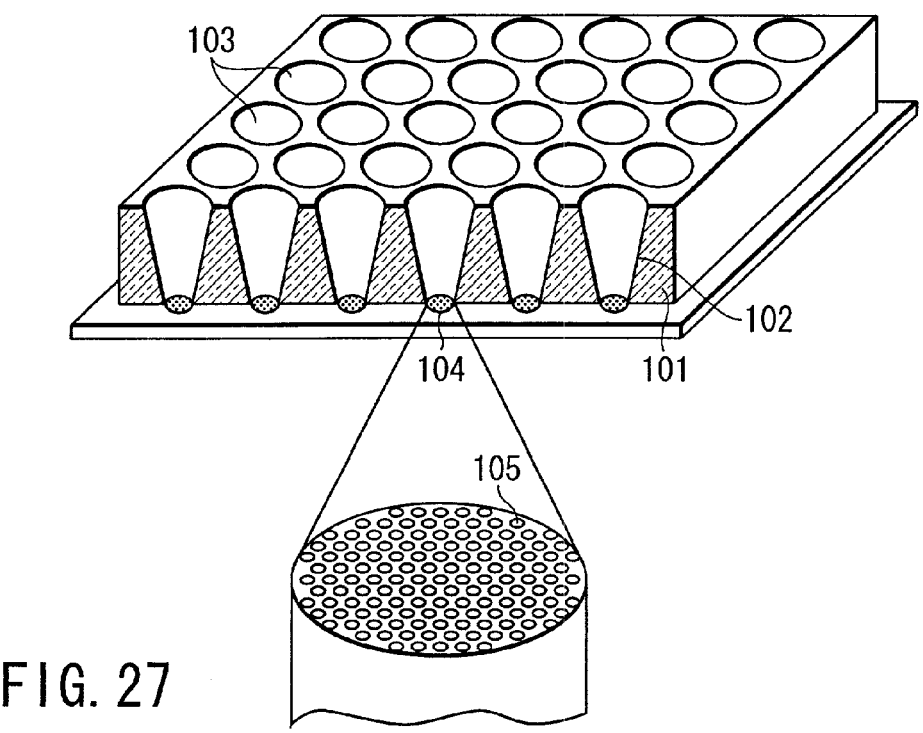
FIG. 27 is a diagram showing a tapered sample well array constituting a three-dimensional array according to a conventional example.

FIGS. 2A and 2B are diagrams showing a schematic configuration of the array for biochemical examination for use in the first embodiment. FIG. 2A is a diagram showing a format of an upper surface, and FIG. 2B is a partial side view. The array for biochemical examination 1 comprises the three-dimensional array shown in FIG. 27. As shown in FIG. 2A, in the array for biochemical examination 1, probe array elements 3 are arranged in two dimensions, and array elements for position detection 2 are disposed in four corners. These probe array elements 3 and array elements for position detection 2 comprise tapered wells 103 as shown in FIG. 27. Each tapered well includes a channel 104 having a diameter of 0.1 to 10 μm in the bottom thereof, and each channel 104 has a large number of micro through holes 105 as shown in FIG. 2B. Probes 31 are bonded to a wall surface of each through hole 105.

That is, in the array for biochemical examination 1, in order to secure bonding reaction of the probe, a solution of the probe is preferably supplied to the different tapered wells 103 on the surface of a porous glass wafer 101. The probes contained in the solution may be held in the respective through holes 105 of the channels 104 disposed in the porous glass wafer 101. Instead of disposing the porous glass wafer 101, a micro amount of the solution of the probe may be pipetted and held directly in each through hole 105. A member including the through holes 105 is constituted as a reaction carrier having a solid structure formed of a porous or fibrous material or a molded material.

Figure 3:
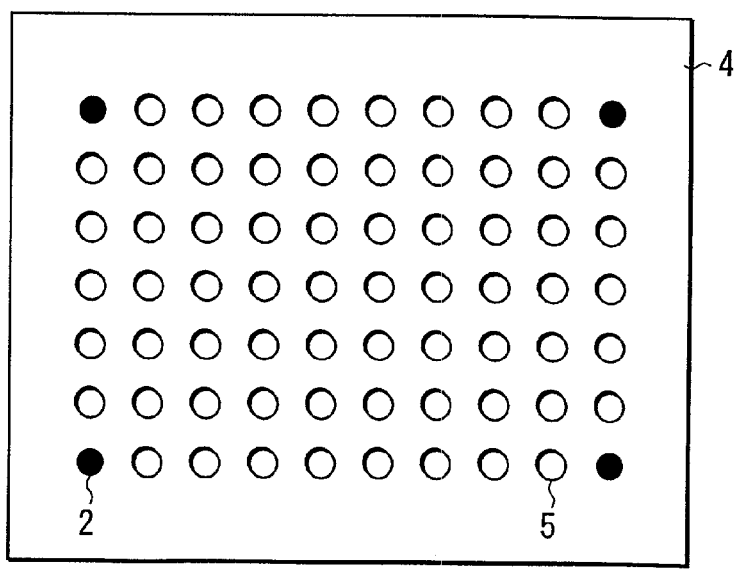
FIG. 3 is a diagram showing a format of a reference array according to the first embodiment of the present invention.

FIG. 3 is a diagram showing the format of the upper surface of the reference array for use in the first embodiment. The reference array 4 comprises the three-dimensional array which can hold fluorescent molecules. As shown in FIG. 3, in the reference array 4, elements for holding the fluorescent molecules 5 are arranged in two dimensions, and the array elements for position detection 2 are disposed in four corners.

As shown in FIGS. 2A, 3, the array for biochemical examination 1 and reference array 4 have the same format. Four array elements for position detection 2 positioned in four corners are present in the same positions in the array for biochemical examination 1 and reference array 4, and are used in positioning the array for biochemical examination 1 and reference array 4 on a stage (not shown) under a microscope. Therefore, the positions of the array elements for position detection 2 are not limited to the positions shown in FIGS. 2A, 3, and may be any positions as long as the elements are present in the same positions in both the arrays. Of course, the formats of the array for biochemical examination 1 and reference array 4 may be optional as long as these conditions are satisfied.

An outline of the biochemical examination in the first embodiment will be described hereinafter.

First, an examiner spots the same number $n_{RM}$ of fluorescent molecules as that of the fluorescent molecules for use as a marker in a substrate for the array in the respective elements for holding the fluorescent molecules 5, and spots fluorescent molecules having a luminescent wavelength different from that of the marker in the respective array elements for position detection 2 so that the reference array 4 is manufactured. Here, an affixed character R means a reference, and an affixed character M denotes a fluorescent material.

Subsequently, the reference array 4 positioned and disposed under microscope observation is irradiated with an excitation lighting, and a fluorescent image is photographed as a reference fluorescent image in the CCD camera 19. The same number of reference fluorescent images as the number of types of fluorescent materials for use in the marker are photographed. Additionally, to prevent the fluorescent material from being deteriorated, it is preferable to cut off the excitation lighting by the shutter 12 immediately after the image is photographed.

Subsequently, the examiner discharges the reference array 4, and disposes the array for biochemical examination 1 in the same position. In the array for biochemical examination 1, the fluorescent molecules having the luminescent wavelength different from that of the marker are held in the array elements for position detection 2 of the substrate for the array, and the corresponding probe solution is similarly held in the probe array element 3 in each solid phase.

Subsequently, the examiner supplies the solution of the sample to be examined labeled by the fluorescent molecule into the array for biochemical examination 1, causes the bonding reaction of the respective probes with the materials in the sample solution, and removes non-bonded materials from the probe array elements 3.

Next, the array for biochemical examination 1 is irradiated with the excitation lighting, and the fluorescent image is photographed as a sample fluorescent image by the CCD camera 19. Similarly as the reference fluorescent images, the same number of sample fluorescent images as the number of types of fluorescent materials for use in the marker are photographed. Additionally, to prevent the fluorescent material from being deteriorated, it is preferable to cut off the excitation light by the shutter 12 immediately after the image is photographed.

Subsequently, the reference fluorescent image and sample fluorescent image are divided into respective element units, and a plurality of divided images are obtained. The number of existing divided images is the number of types of fluorescent materials for use in the marker×the number of probe array elements×2. Additionally, in this case, dividing conditions are determined by a coordinate of a gravity center position of four array elements for position detection 2 or a centroid position of a binarized image, and the known array format.

Additionally, when the image is formed on a light receiving element having a γ value of 1 by a non-aberration lens, a binarized point in a ½ level of a maximum signal level may be considered to be an intersection of a main beam and optimum image plane. Therefore, all the divided images are binarized in the ½ level of the maximum signal level, a region of the binarized image is set, and a maximum x coordinate, minimum x coordinate, maximum y coordinate and minimum y coordinate of the region are obtained.

For the reference binarized image, it is assumed that the maximum x coordinate is $x_{RMkmax}$, the minimum x coordinate is $x_{RMkmin}$, the maximum y coordinate is $y_{RMkmax}$ and the minimum y coordinate is $y_{RMkmin}$. For the sample binarized image, it is assumed that the maximum x coordinate is $x_{SMkmax}$, the minimum x coordinate is $x_{SMkmin}$, the maximum y coordinate is $y_{SMkmax}$ and the minimum y coordinate is $y_{SMkmin}$. Additionally, only for the divided image of the sample fluorescent image, a real area of the binarized image is calculated as $S_{Mk}$.

Figure 4:
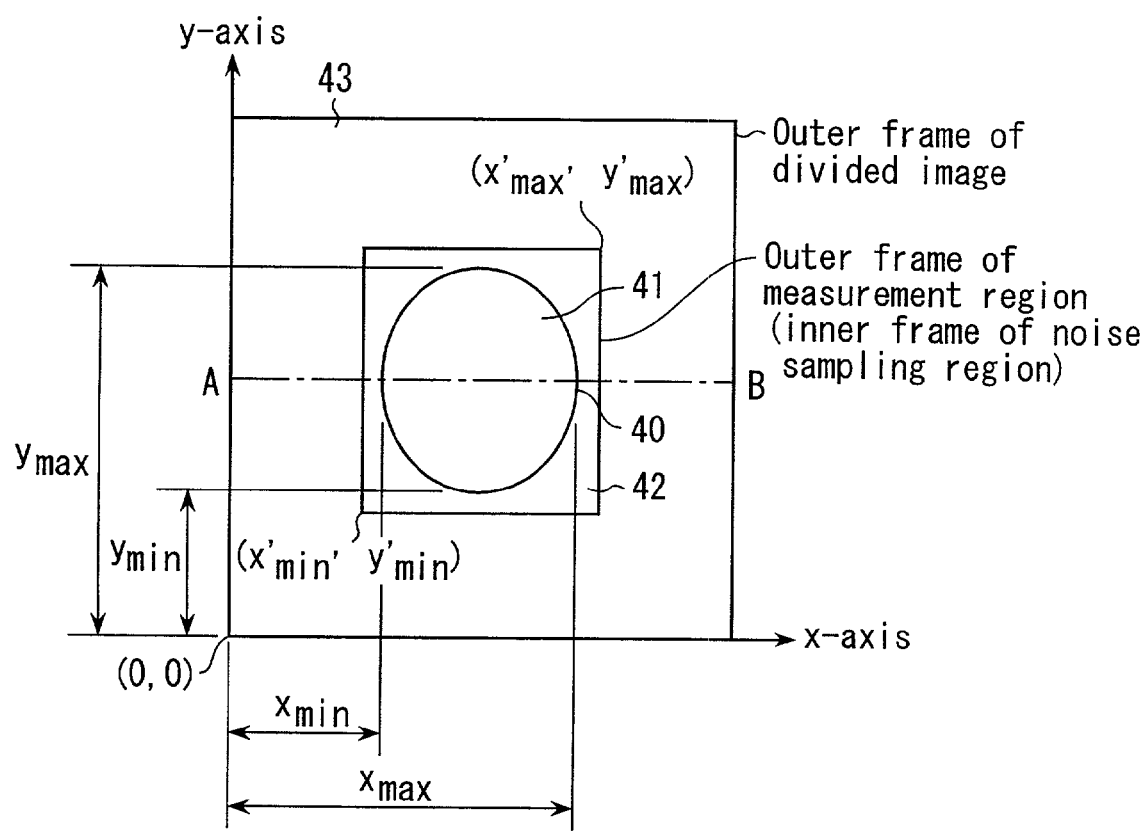
FIG. 4 is a diagram showing a divided image of a reference fluorescent image and sample fluorescent image according to the first embodiment of the present invention.
Figure 5:
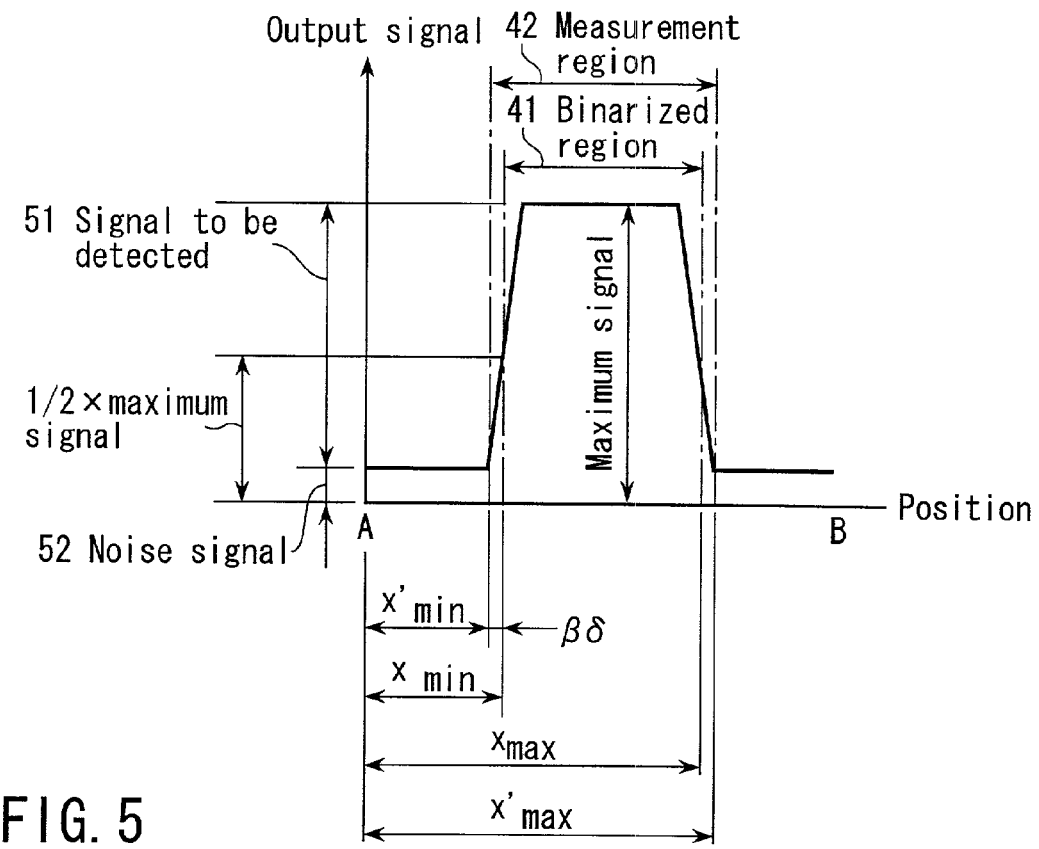
FIG. 5 is a diagram showing an output signal from CCD according to the first embodiment of the present invention.

FIG. 4 is a diagram showing the divided image of the reference fluorescent image and sample fluorescent image, and FIG. 5 is a diagram showing an output signal from CCD on a line segment AB shown in FIG. 4. A relation of a binarized region 41 with a maximum x coordinate $x_{max}$, minimum x coordinate $x_{min}$, maximum y coordinate $y_{max}$ and minimum y coordinate $y_{min}$ of the region is shown in FIGS. 4 and 5. Additionally, in the drawings, affixed characters RMk and SMk do not have to be distinguished, and are therefore omitted.

Subsequently, two coordinates to give a rectangular region for determining a measurement region 42 and noise sampling region 43 are set at $(x'_{min}, y'_{min})$ and $(x'_{max}, y'_{max})$ as shown in FIGS. 4 and 5, and $x'_{min}$, $y'_{min}$, $x'_{max}$ and $y'_{max}$ are given by the following equations.

$$x'_{RMkmin} = x_{RMkmin} - \beta\delta \quad x'_{SMkmin} = x_{SMkmin} - \beta\delta \quad (1)$$

$$y'_{RMkmin} = y_{RMkmin} - \beta\delta \quad y'_{SMkmin} = y_{SMkmin} - \beta\delta \quad (2)$$

$$x'_{RMkmax} = x_{RMkmax} + \beta\delta \quad x'_{SMkmax} = x'_{SMkmax} + \beta\delta \quad (3)$$

$$y'_{RMkmax} = y_{RMkmax} + \beta\delta \quad y'_{SMkmax} = y'_{SMkmax} + \beta\delta \quad (4)$$

Additionally, β denotes an image magnification of optics, and δ is given by the following equation.

$$\delta = 1.619\frac{\lambda}{a} + a|\Delta| \quad (5)$$

Here, λ denote a fluorescent wavelength of a marker M to be detected, a denotes a numerical aperture on a sample side, and Δ denotes a defocus amount. Moreover, a first term of a right side denotes a distance (blur amount by diffraction) between a center of a diffraction image and a bottom between a secondary diffraction peak and a tertiary diffraction peak, and a second term denotes a blur amount (blur amount by defocus) attributed to a focusing error. That is, equation (5) may be considered as an equation which gives a maximum blur amount in consideration of the focusing error.

Additionally, as shown in FIG. 5, the divided image is formed by a synthesized signal of a signal to be detected 51 and noise signal 52. A noise depends on an apparatus configuration and measurement environment, but an excitation light noise (noise attributed to the excitation light) is generally dominant, and a stray light noise (noise attributed to a light source other than the excitation light) cannot sometimes be ignored. Moreover, the excitation light noise includes a reflected light noise of the excitation light on the substrate, and a self luminescent noise of the substrate by the excitation light.

Figure 6:
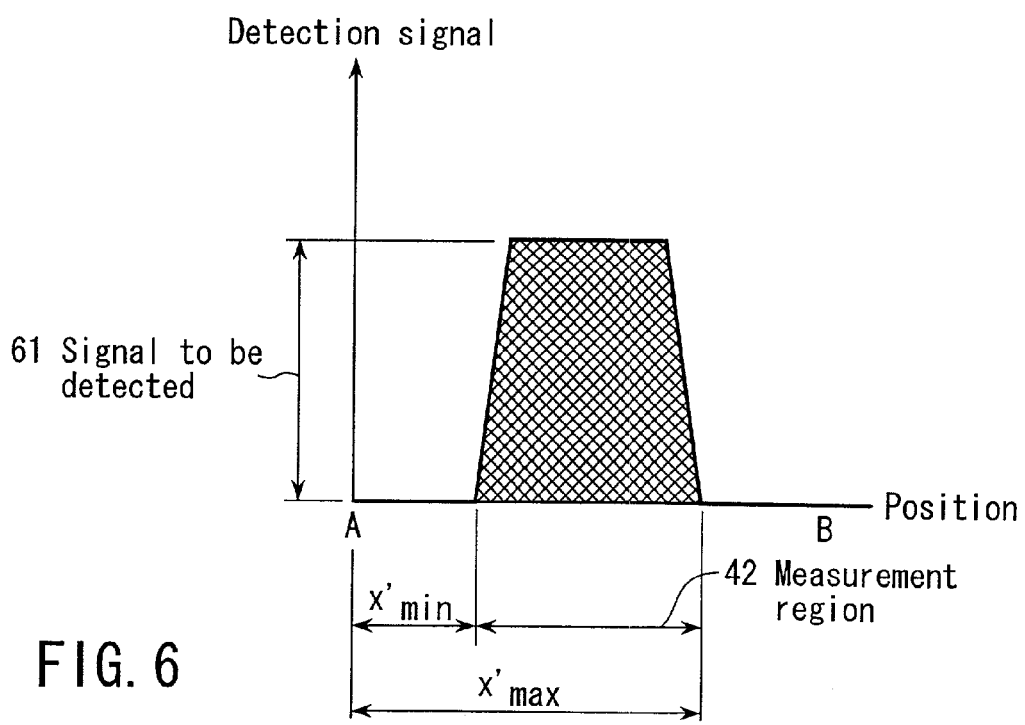
FIG. 6 is a diagram showing a signal obtained by subtracting a noise signal from the output signal according to the first embodiment of the present invention.

FIG. 6 is a diagram showing a signal obtained by subtracting the noise signal from the output signal. By this subtraction processing, a signal to be detected 61 can be extracted. Additionally, in FIGS. 4 to 6 the signals are modeled and represented for ease of description, but the signal to be detected and the noise signal are not actually flat, and there is unevenness in some position. Particularly the excitation light noise reflects lighting unevenness, and is therefore a maximum cause for the unevenness of the noise signal.

In the first embodiment, even when the binarized region is not circular because of the unevenness of the signal to be detected as shown in FIG. 4, or even when a plurality of binarized regions are present in one divided image, the rectangular region determined by $(x'_{min}, y'_{min})$ and $(x'_{max}, y'_{max})$ is used as the measurement region. It is therefore guaranteed that all the signals to be detected are included in the measurement region.

Then, in the first embodiment, on the assumption of the unevenness of the noise signal, an average noise signal in the noise sampling region 43 is subtracted from the signal of the measurement region 42, and a detection signal shown in FIG. 6 is obtained. The average noise signal is obtained by dividing a total sum of the signals in the noise sampling region by the area of the noise sampling region. Subsequently, the total sum of the detection signals obtained by the subtraction in the measurement region 42 is used as a signal intensity of each array element.

According to the method, it is possible to sample the noise signal in the vicinity of the signal to be detected, so that a detection precision of the signal to be detected is enhanced. Additionally, the measurement region is set in consideration of defocus as described above, and it is therefore apparent that any defocus noise is not generated.

As described above, a quantity of the obtained signal intensity is the number of types of fluorescent materials for use in the marker×the number of probe array elements×2. Now, the signal intensities of the probe array element 3 and element for holding the fluorescent molecule 5 are represented by $P_{RMk}$ and $P_{SMk}$, respectively. Here, the affixed characters R and S denote the reference and sample, respectively, M is an affixed character corresponding to the fluorescent material, and k denotes the number of the element for holding the fluorescent molecule 5 as well as the number of the corresponding probe array element 3.

Subsequently, the signal intensity $P_{SMk}$ of the probe array element 3 is corrected with the area of the probe array element 3, and $P_{Mk}$ is obtained. This $P_{Mk}$ is obtained by the following equation.

$$P_{Mk} = \frac{S_0}{S_{Mk}} P_{SMk} \quad (6)$$

Here, $S_0$ denotes a standard area of the probe array element 3, and $S_{Mk}$ denotes the real area of the binarized image of each probe array element 3 calculated beforehand. By this correction, the noise by the probe pipetting error can be removed.

Subsequently, the intensity signal $P_{Mk}$ of each probe array element 3 of the sample fluorescent image is represented by the number $n_{Mk}$ of fluorescent molecules (or chemical luminescent molecules) of the marker M present in the probe array element 3 as follows.

$$P_{Mk} = I_{Mk}\left\{n_{Mk} - \rho\left(\sum_{M'=1}^{J} n_{M'k} - 1\right)\right\} \quad (7)$$

Additionally, ρ is a nonlinear coefficient of a luminescent function of fluorescence and is given by a constant. Moreover, $I_{Mk}$ can be represented by the following equation.

$$I_{Mk} = \frac{P_{RMk}}{n_{RM} - \rho\left(\sum_{M'=1}^{J} n_{RM'} - 1\right)} \quad (8)$$

Here, $n_{RM}$ denotes the number of fluorescent molecules (or chemical luminescent molecules) of the marker M present in the element for holding the fluorescent molecule 5 of the number k of the reference array 4.

Therefore, $I_{Mk}$ is obtained by the equation (8), and the equation (7) can be used to obtain the number $n_{Mk}$ of the fluorescent molecules (or the chemical luminescent molecules) of the marker M present in the probe array element 3. That is, the corresponding number of equations are made from the detected values of the signal intensities $P_{Mk}$ of the marker materials for each probe array element 3, the detected values being equal to the number of the marker materials. These equations are solved and thereby the number $n_{Mk}$ of the fluorescent molecules (or the chemical luminescent molecules) of the marker M present in the probe array element 3 is obtained. By the equations (7) and (8), the following equation is obtained.

$$n_{Mk} = \frac{P_{Mk}\left\{n_{RM} - \rho\left(\sum_{M'=1}^{J} n_{RM'} - 1\right)\right\}}{P_{RMk}} + \rho\left(\sum_{M'=1}^{J} n_{M'k} - 1\right) \quad (9)$$

When the nonlinear coefficient ρ is regarded as 0 in the equation (8), $I_{Mk}$ denotes the signal intensity per one fluorescent molecule (or the chemical luminescent molecule). In this case, the equation (9) becomes very simple and $n_{Mk}$ is obtained by the following equation.

$$n_{Mk} = \frac{P_{Mk} n_{RM}}{P_{RMk}} \quad (10)$$

A way of obtaining $n_{Mk}$ by successive approximation when the nonlinear coefficient ρ is not regarded as 0 will next be described. In the equation (9), an approximate value of i-th $n_{Mk}$ is represented by $n_{Mk}^{(i)}$, and the approximate value of i–1-th $n_{Mk}$ is used in $n_{Mk}$ of the right side. This is represented by the following equation.

$$n_{Mk}^{(i)} = \frac{P_{Mk}\left\{n_{RM} - \rho\left(\sum_{M'=1}^{J} n_{RM'} - 1\right)\right\}}{P_{RMk}} + \rho\left(\sum_{M'=1}^{J} n_{M'k}^{(i-1)} - 1\right) \quad (11)$$

Additionally, i=1, 2, 3 . . . Moreover, the following is given as an initial value of $n_{Mk}$.

$$n_{Mk}^{(0)} = 0 \quad (12)$$

Furthermore, the following equation may be given as a convergence condition.

$$\sum_{M=1}^{J} (n_{Mk}^{(i)} - n_{Mk}^{(i-1)})^2 < 1 \quad (13)$$

That is, $n_{Mk}^{(i)}$ is equal to $n_{Mk}$, when the equation (13) is satisfied.

Figure 7:
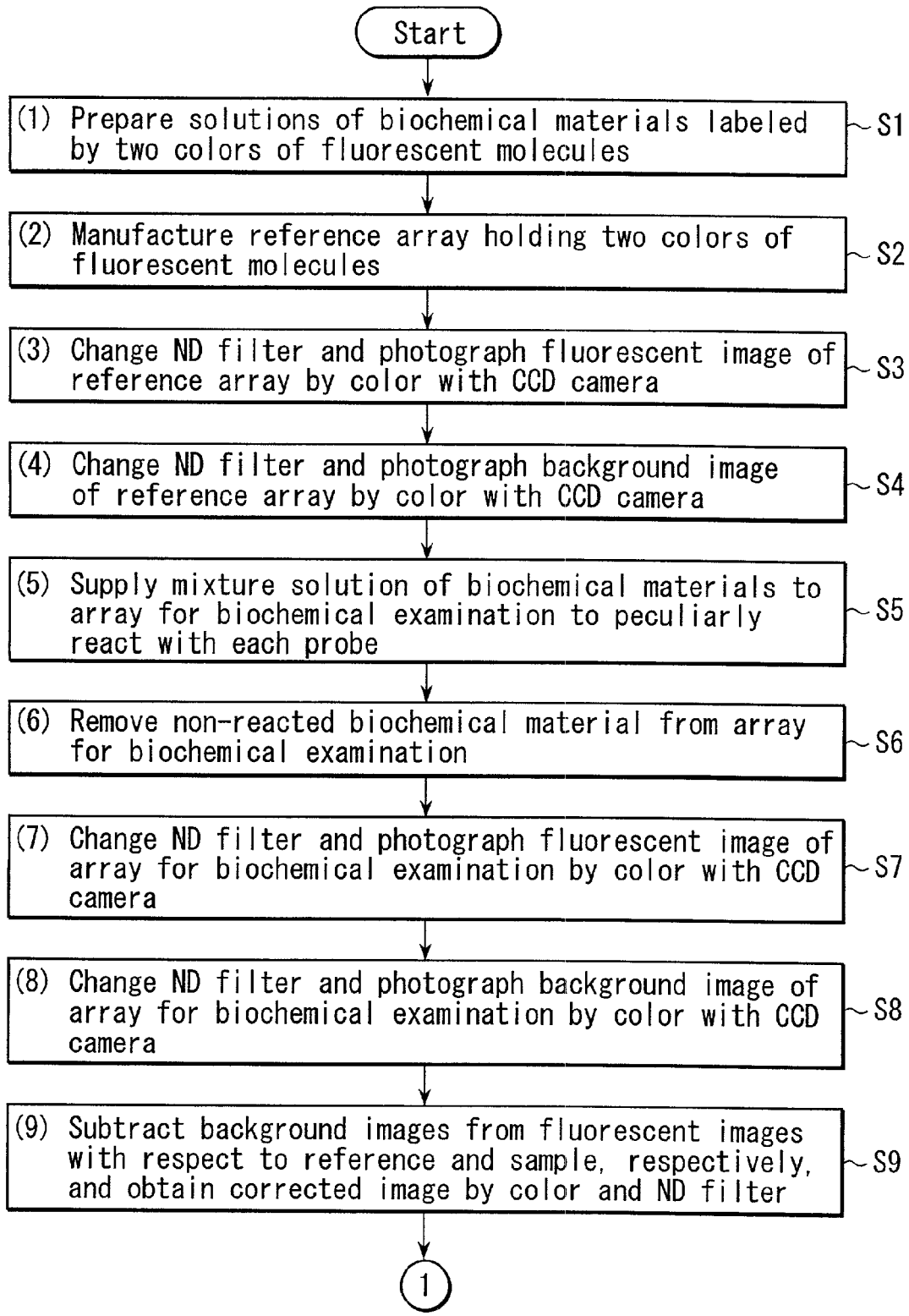
FIG. 7 is a flowchart showing an examination procedure according to the first embodiment of the present invention.
Figure 8:
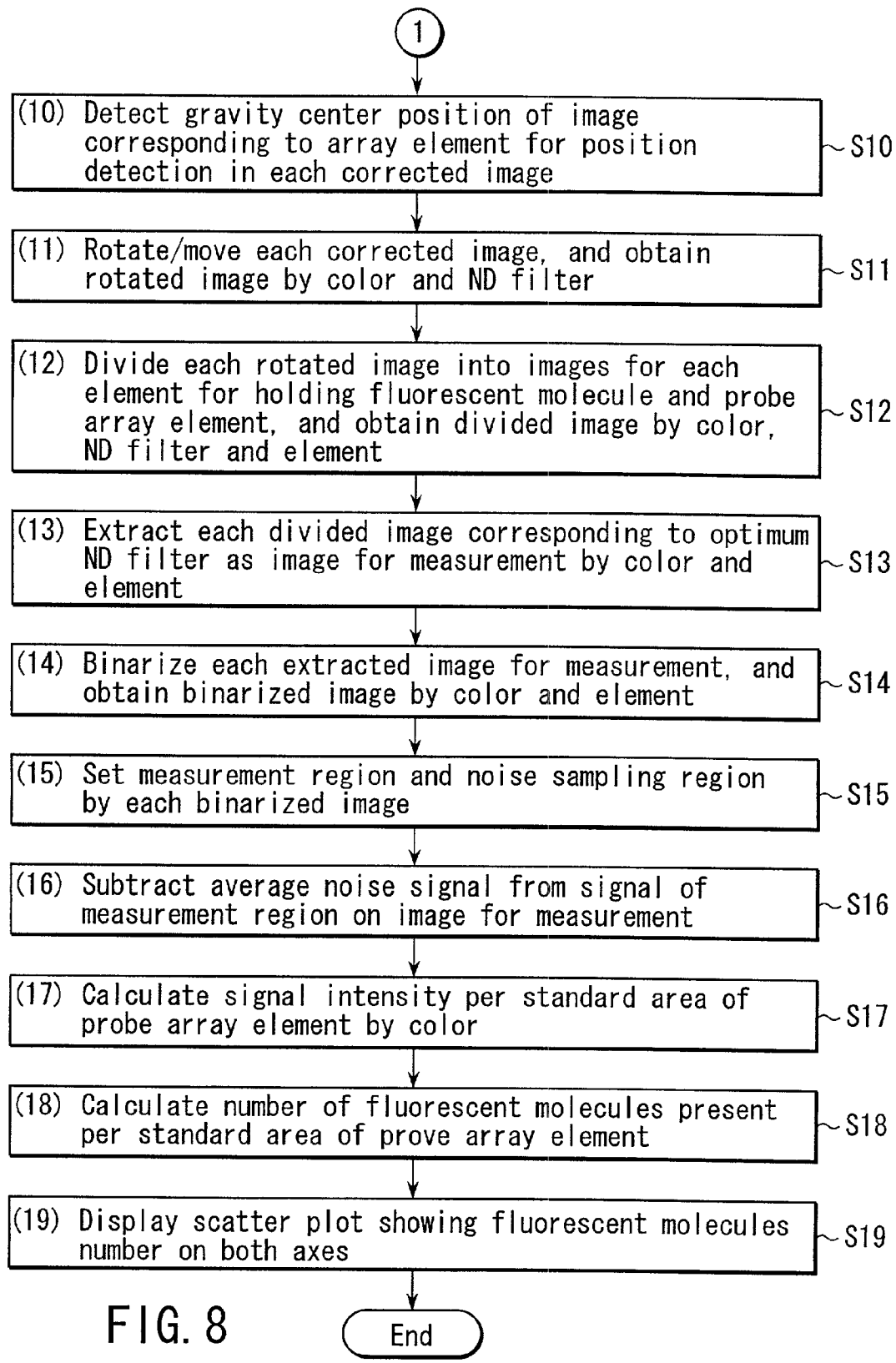
FIG. 8 is a flowchart showing the examination procedure according to the first embodiment of the present invention.

FIGS. 7 and 8 are flowcharts showing an examination procedure according to the first embodiment. Examination method and action will be described hereinafter with reference to FIGS. 7, 8.

(1) Step S1: First, the examiner prepares solutions of two types of biochemical materials labeled by two colors of fluorescent molecules. In this case, the examiner prepares the solutions of two types of biochemical materials to be compared with the same concentration, and labels one of the solutions with FITC, and the other with rhodamine. These marker materials may be any other combination of materials different from each other in the fluorescent wavelength. Thereafter, the prepared solutions of two types of biochemical materials are mixed and stirred at a ratio of 1:1, and a mixture solution of the biochemical materials is obtained. The mixture ratio may be changed in accordance with properties of solutions of two types of biochemical materials and the marker materials.

(2) Step S2: The examiner manufactures the reference array 4 which holds two colors of fluorescent molecules. In this case, the examiner spots the same fluorescent molecule number $n_{RM}$ of FITC and rhodamine for use as the fluorescent markers in the substrate for the array in the elements for holding the fluorescent molecules 5, and spots the fluorescent molecules having the luminescent wavelength different from that of the marker in the array elements for position detection 2 so that the reference array 4 is manufactured. In this case, the spotted positions correspond to the positions of the probe array elements 3. Here, the affixed character R denotes the reference, and the affixed character M denotes the fluorescent material.

Additionally, a spotting method comprises: specifying the fluorescent molecule number for use from the weight of the fluorescent molecules for use and the molecular weight; preparing a predetermined amount of solution of fluorescent molecules by the fluorescent molecules number; and ejecting the solution onto the substrate for the array by an ink jet system. The fluorescent molecule number $n_{RM}$ per one element is calculated and obtained from the miscellaneous amounts (the solution amount and the fluorescent molecules number in the solution) and the ejected amount of the solution. Additionally, for a holding method of the fluorescent molecules, when a solid phase reagent is used, the molecules can securely be held, but the reagent is not necessarily required.

(3) Step S3: The examiner changes the ND filter 17 on an observation light path a, and photographs the fluorescent image of the reference array 4 for each color with the CCD camera 19. In this case, the reference array 4 is excited/lightened with the excitation light source 11, and the fluorescent image generated by the fluorescent molecule in each element for holding the fluorescent molecule 5 is photographed with the CCD camera 19. In this case, the examiner switches/operates the excitation filter unit 140 and disposes the excitation filter 14 corresponding to the desired color of the fluorescent molecule on a lighting path b. Furthermore, the examiner switches/operates the ND filter unit 170 and disposes the desired ND filter 17 on the observation light path a.

The excitation light from the excitation light source 11 is passed through the lens 13 and excitation filter 14 and reflected by the dichroic mirror 15. The whole upper surface of the reference array 4 is irradiated via the objective lens 16. The fluorescent light generated from the reference array 4 is incident upon the CCD camera 19 via the objective lens 16, dichroic mirror 15, ND filter 17, and image forming lens 18, and the fluorescent image is photographed for each color of the fluorescent molecule. Therefore, in this step, the number of obtained fluorescent images is 2 colors×the number of ND filters. The fluorescent images photographed with the CCD camera 19 are sent to the image processor 20.

Additionally, the CCD is used as a light receiving element in the first embodiment, but the CCD is not limited, and any other area sensor may be used. Therefore, the "CCD" described below may be the "area sensor".

(4) Step S4: The examiner changes the ND filter 17 on the observation light path a, and photographs the background image of the reference array 4 for each color of the fluorescent molecule with the CCD camera 19. In this case, immediately after the fluorescent image of the reference array 4 is photographed, the excitation lighting is cut off by the shutter 12, and the CCD camera 19 takes the background image. The number of background images is the same as the number of fluorescent images. The background image is constituted of a dark current noise and stray light noise unnecessary for a detection intensity. The background image photographed with the CCD camera 19 is sent to the image processor 20.

(5) Step S5: The examiner supplies the mixture solution of the biochemical materials into the array for biochemical examination 1, and allows the solution to peculiarly react with each probe. In this case, the examiner disposes the array for biochemical examination 1 shown in FIG. 2A on the sample surface under observation of the fluorescent microscope shown in FIG. 1, and supplies the mixture solution of the biochemical materials uniformly onto the surface. This causes a peculiar bonding reaction between the probes in the probe array elements 3 on the array for biochemical examination 1 and the biochemical materials contained in the mixture solution. As a result, the number of fluorescent molecules corresponding to an intensity of the reaction are indirectly bonded to the probes in each probe array element 3.

(6) Step S6: The examiner removes the non-reacted biochemical materials from the array for biochemical examination 1. In this case, after the bonding reaction, the examiner removes the non-bonded biochemical materials from the respective probe array elements 3 of the array for biochemical examination 1. In general, a method of using a wash solution to wash the array is used. However, when the reaction carrier has a solid structure, the solution including the materials may be removed by a pump without using the wash solution. Additionally, needless to say, the materials can securely be removed, when the wash solution is used.

(7) Step S7: The examiner changes the ND filter 17 on the observation light path a, and photographs the fluorescent image of the array for biochemical examination 1 according to the color with the CCD camera 19. In this case, the array for biochemical examination 1 is excited/lightened with the excitation light source 11, and the fluorescent image generated by the fluorescent molecule in each probe array element 3 is photographed with the CCD camera 19. In this case, the examiner switches/operates the excitation filter unit 140 and disposes the excitation filter 14 corresponding to the desired color of the fluorescent molecule on the lighting path b. Furthermore, the examiner switches/operates the ND filter unit 170 and disposes the desired ND filter 17 on the observation light path a.

The excitation light from the excitation light source 11 is passed through the lens 13 and excitation filter 14 and reflected by the dichroic mirror 15. The whole upper surface of the array for biochemical examination 1 is irradiated via the objective lens 16. The fluorescent light generated from the array for biochemical examination 1 is incident upon the CCD camera 19 via the objective lens 16, dichroic mirror 15, ND filter 17, and image forming lens 18, and the fluorescent image is photographed by the color of the fluorescent molecule. The number of the fluorescent images of the array for biochemical examination 1 is the same as corresponding number of the background images or the fluorescent images of the reference array 4. The fluorescent images photographed by the CCD camera 19 are sent to the image processor 20.

(8) Step S8: The examiner changes the ND filter 17 on the observation light path a, and photographs the background image of the array for biochemical examination 1 by the color of the fluorescent molecule with the CCD camera 19. In this case, immediately after the fluorescent image of the array for biochemical examination 1 is photographed, the excitation lighting is cut off by the shutter 12, and the CCD camera 19 takes the background image. The number of background images of the array for biochemical examination 1 is the same as the number of fluorescent images. Similarly as the background image of the reference array 4, the background image is constituted of the dark current noise and stray light noise unnecessary for the detection intensity. The background image photographed by the CCD camera 19 is sent to the image processor 20.

(9) Step S9: The image processor 20 subtracts the respective background images from the fluorescent images of the reference and sample, and obtains corrected images by color and ND filter. In general, an output of the light receiving element includes direct-current noises such as the dark current noise and stray light noise. In order to remove the direct-current noises, the background image is subtracted from the fluorescent image with respect to the reference array 4 and array for biochemical examination 1, and the corrected image is obtained as an object of the subsequent processing. Therefore, in this step, the number of obtained corrected images is 2 colors×the number of ND filters. Additionally, the fluorescent image and background image are unnecessary thereafter.

(10) Step S10: The image processor 20 detects the gravity center position of the image corresponding to the array element for position detection 2 in each corrected image. As shown in FIGS. 2A and 3, the array elements formed in the array for biochemical examination 1 and reference array 4 are arranged in a two-dimensional manner, and four array elements positioned in four corners are used as the array elements for position detection 2. The other array elements are used as the probe array elements 3 or the elements for holding the fluorescent molecules 5.

Since the array elements for position detection 2 are constituted to emit position signals, the materials in the elements may be any luminescent material or reflective material, but the fluorescent materials having fluorescent wavelengths different from the fluorescent wavelengths of two colors for use are preferably used. This is because a possibility of action of the fluorescent light generated from the array element for position detection 2 as the noise can be eliminated. In this case, the element is lightened with the excitation wavelength for position detection, and the positions are detected.

(11) Step S11: The image processor 20 rotates/moves each corrected image, and obtains rotated images for the respective colors and ND filters. In this case, the position coordinate is corrected in such a manner that each quadrangle formed by four position coordinates obtained with respect to the reference array 4 and array for biochemical examination 1 becomes rectangular with a minimum deviation. Subsequently, each corrected image is rotated/moved around each image center as a rotation center so that each side of the rectangle extends in parallel to the coordinate axis. The moved image will be referred to as the rotated image. Additionally, the corrected images are unnecessary thereafter.

(12) Step S12: The image processor 20 divides the rotated image into images for respective elements for holding the fluorescent molecules 5 and probe array elements 3, and obtains the divided images by the color, ND filter and element.

In this case, the image processor 20 determines dividing conditions from four position coordinates of each rotated image of the reference array 4 and array for biochemical examination 1 and the arrangement conditions of the elements for holding the fluorescent molecules 5 and probe array elements 3. On the dividing conditions, all the rotated images are divided into images for the respective elements for holding the fluorescent molecules 5 or the probe array elements 3, and divided images are obtained. Additionally, the divided image of the rotated image of the reference array 4 will be referred to as a reference divided image, and the divided image of the rotated image of the array for biochemical examination 1 will be referred to as a sample divided image. Therefore, in this step, the number of obtained divided images is 2×the number of ND filters×the number of probe array elements. Additionally, the rotated images are unnecessary thereafter.

(13) Step S13: The image processor 20 extracts each divided image corresponding to the optimum ND filter 17 as an image for measurement by color and element.

In this case, the image processor 20 extracts one reference divided image whose maximum signal intensity is in a dynamic range and whose signal intensity is maximum from the same number of reference divided images as the number of ND filters of the element for holding the fluorescent molecule 5 which have the same color in the same position. This will be referred to as a reference image for measurement. Similarly, the image processor 20 extracts one sample divided image whose maximum signal intensity is in the dynamic range and whose signal intensity is maximum from the same number of sample divided images as the number of ND filters of the probe array element 3 which have the same color in the same position. This will be referred to as a sample image for measurement.

(14) Step S14: The image processor 20 binarizes each extracted image for measurement, and obtains the binarized images by color and element. All the reference images for measurement and sample images for measurement are binarized at a ½ level of the maximum signal, and a reference binarized image and sample binarized image are obtained, respectively. For the sample binarized image, the area $S_{MK}$ of the binarized region 41 is calculated.

(15) Step S15: The image processor 20 sets the measurement region 42 and noise sampling region 43 by each binarized image.

In this case, the image processor 20 obtains the maximum x coordinate $x_{RMkmax}$, minimum x coordinate $x_{RMkmin}$, maximum y coordinate $y_{RMkmax}$ and minimum y coordinate $y_{RMkmin}$ with respect to all the reference binarized images. Similarly, the processor obtains the maximum x coordinate $x_{SMkmax}$, minimum x coordinate $x_{SMkmin}$, maximum y coordinate $y_{SMkmax}$ and minimum y coordinate $y_{RMkmin}$ with respect to all the sample binarized images. Then, the processor calculates the coordinates $x'_{RMkmax}$, $x'_{RMkmin}$, $y'_{RMkmax}$, $y'_{RMkmin}$, $x'_{SMkmax}$, $x'_{SMkmin}$, $y'_{SMkmax}$ and $y'_{SMkmin}$ to set the sampling region of the noise.

Moreover, a region in a rectangle determined by points $(x'_{RMkmin}, y'_{RMkmin})$ and $(x'_{RMkmax}, y'_{RMkmax})$ is obtained as the measurement region of the reference image for measurement, and a region outside the rectangle is obtained as the noise sampling region of the reference image for measurement. Similarly, a region in the rectangle determined by points $(x'_{SMkmin}, y'_{SMkmin})$ and $(x'_{SMkmax}, y'_{SMkmax})$ is obtained as the measurement region of the sample image for measurement, and a region outside the rectangle is obtained as the noise sampling region of the sample image for measurement.

(16) Step S16: The image processor 20 subtracts the average noise signal from the signal of the measurement region 42 on the image for measurement.

In this case, the image processor 20 obtains the noise per unit area from the signal of the noise sampling region 43 of the reference image for measurement, subtracts the signal from the signal of the measurement region 42 of the reference image for measurement and obtains a detection signal of the reference image. Similarly, the processor obtains the noise per unit area from the signal of the noise sampling region 43 of the sample image for measurement, subtracts the signal from the signal of the measurement region 42 of the sample image for measurement and obtains a detection signal of the sample image.

(17) Step S17: The image processor 20 calculates the signal intensity per standard area of the probe array element 3 by color.

In this case, the image processor 20 calculates the total sum of the detection signals in the measurement regions 42 of each element for holding the fluorescent molecule 5 as $P_{RMk}$. Similarly, the processor calculates the total sum of the detection signals in the measurement regions 42 of each probe array element 3 as $P_{SMk}$. Subsequently, the processor uses the equation (6) to calculate the signal intensity per standard area $S_0$ of the probe array element 3 for each color. These signal intensities are obtained as intensities from which intensity errors caused by the excitation light unevenness, excitation light noise and pipetting error of the probe are removed.

(18) Step S18: The image processor 20 calculates the number of fluorescent molecules (or the chemical luminescent molecules) present per standard area of the probe array element 3 for each color. In this case, the image processor 20 uses the equations (11), (12) and (13) to calculate the fluorescent molecules number $n_{Mk}$ present per standard area $S_0$ of the probe array element 3 for each color from the signal intensity per standard area $S_0$ of the probe array element 3.

(19) Step S19: The image processor 20 displays a scatter plot indicating the number of fluorescent molecules (or the chemical luminescent molecules) calculated for each color on both axes. In this case, the image processor 20 displays the scatter plot indicating the fluorescent molecules numbers of each probe array element 3 for two colors of fluorescent materials on x-axis and y-axis in the display 21.

Figure 9:
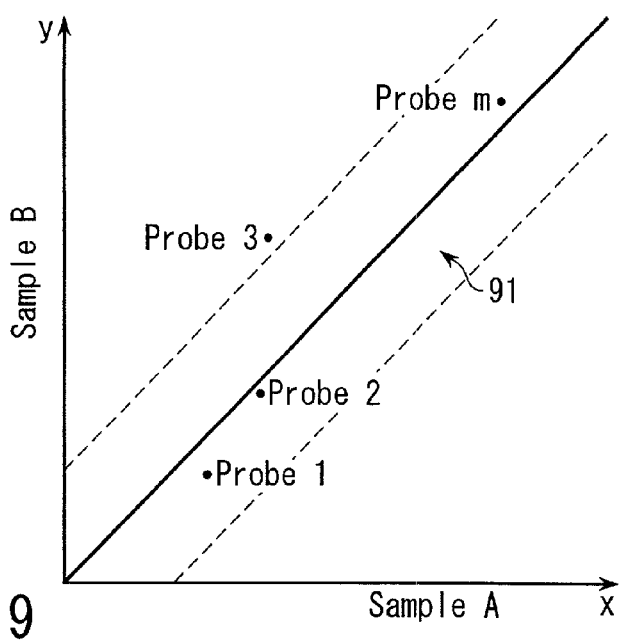
FIG. 9 is a scatter plot according to the first embodiment of the present invention.

FIG. 9 shows an example of the scatter plot, and x-axis indicating the fluorescent molecules number of sample A and y-axis indicating the fluorescent molecules number of sample B are shown on a logarithmic scale. FIG. 9 schematically shows the respective probes of m probe array elements 3. For the probes other than "probe 3", a balance of the fluorescent molecules number between the sample A and B is in a range 91 (between two broken lines). In this case, the samples A and B are judged to have the same degree of bonding reaction with the probe. For the probe 3, it is judged that the reaction of the sample B is apparently stronger than the reaction of the sample A. Additionally, the x and y axes are both logarithm axes, two broken lines to determine the range 91 are represented by $y=m_n x$ and $y=(1/m_n)x$, and a solid line is represented by a line of $y=x$. Three straight lines are mathematically parallel to one another. To set a range of ±10% with respect to $y=x$, $m_n$ 1.1 is set, and this value can appropriately set and displayed by the image processor 20. This scatter plot can accurately represent the reaction state of the probe of each probe array element with the sample.

According to the first embodiment, the reference fluorescent image is introduced. Therefore, even when there is spatial unevenness in the excitation lighting, the output can appropriately be corrected. Furthermore, luminescent properties and fluctuation with time of the fluorescent molecules for use are also considered in the method. Therefore, the fluorescent molecules number $n_{Mk}$ of the marker M present for each probe array element, that is, the reaction state of the probe with the object material can accurately be obtained. In this case, the marker is not limited to the fluorescent molecule, and may be luminescent molecules such as the chemical luminescent molecule. Additionally, the photographing of the reference fluorescent image and the photographing of the sample fluorescent image may be performed in reverse order without any problem.

Figure 10:
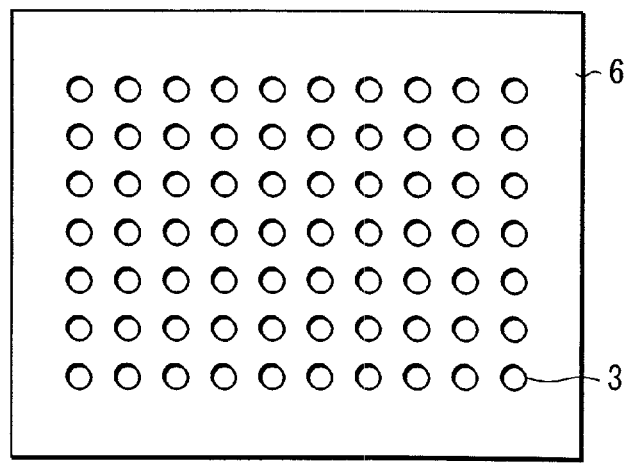
FIG. 10 is a diagram showing a format of an upper surface of the array for biochemical examination for use in a second embodiment of the present invention.

FIG. 10 is a diagram showing the format of the upper surface of the array for biochemical examination for use in a second embodiment of the present invention. An array for biochemical examination 6 shown in FIG. 10 is constituted by replacing four array elements for position detection 2 in the array for biochemical examination 1 shown in FIG. 2A with the respective probe array elements 3.

Figure 11:
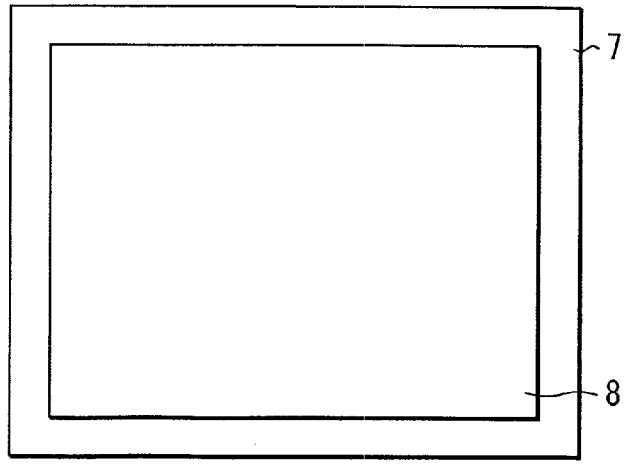
FIG. 11 is a diagram showing the format of the upper surface of the reference array for use in the second embodiment of the present invention.

FIG. 11 is a diagram showing the format of the upper surface of the reference array for use in the second embodiment. A reference array 7 shown in FIG. 11 comprises a three-dimensional array which can hold the fluorescent molecules, and includes one plane of a fluorescent molecule holding region 8. The fluorescent molecule holding region 8 is set to be broader than a region occupied by all the probe array elements 3 shown in FIG. 10. Additionally, the array for biochemical examination 6 and reference array 7 are used instead of the array for biochemical examination 1 and reference array 4 described in the first embodiment The outline of the biochemical examination in the second embodiment will be described hereinafter.

First, the examiner supplies the same fluorescent molecules as those for use as the marker in the substrate for the array to the fluorescent molecule holding region 8 with a homogeneous distribution and manufactures the reference array 7.

Subsequently, the reference array 7 positioned and disposed under the microscope observation is irradiated with the excitation lighting, and the fluorescent image is photographed as the reference fluorescent image in the CCD camera 19. The same number of reference fluorescent images as the number of types of fluorescent materials for use in the marker are photographed. Additionally, to prevent the fluorescent material from being deteriorated, it is preferable to cut off the excitation lighting by the shutter 12 immediately after the image is photographed.

Subsequently, the examiner discharges the reference array 7, and disposes the array for biochemical examination 6 in the same position. In the array for biochemical examination 6, the probe solution is contained beforehand in the probe array element 3 in the solid phase.

Subsequently, the examiner supplies the solution of the sample to be examined labeled by the fluorescent molecule into the array for biochemical examination 6, causes the bonding reaction with the respective probes and materials in the sample solution, and removes the non-bonded materials from the probe array elements 3.

Next, the array for biochemical examination 6 is irradiated with the excitation lighting, and the fluorescent image is photographed as a sample fluorescent image by the CCD camera 19. Similarly as the reference fluorescent images, the same number of sample fluorescent images as the number of types of fluorescent materials for use in the marker are photographed. Additionally, to prevent the fluorescent material from being deteriorated, it is preferable to cut off the excitation lighting by the shutter immediately after the image is photographed. The signal intensity of the sample fluorescent image for each probe array element 3 is represented by $P_{Mk}$. Here, the affixed character M denotes the fluorescent material, and k denotes the number of the probe array element.

Subsequently, the image processor 20 detects the position and real area $S_{Mk}$ of each probe array element 3 by the image processing, uses the equation (6) to calculate $P_{Mk}$, cuts out the signal intensity corresponding to the standard area $S_0$ of the probe array element 3 in the same position as the above-described position from the reference fluorescent image, and represents the signal intensity as $P_{RMk}$. Here, the affixed character R denotes the reference.

Next, when the signal intensity $P_{Mk}$ of each probe array element 3 of the sample fluorescent image is represented by the fluorescent molecules number $n_{Mk}$ of the marker M present in the probe array element 3, the same equation (7) results.

The subsequent processing is similar to that of the first embodiment. Additionally, different from the first embodiment, $n_{RM}$ is unclear in the second embodiment. Therefore, only the constitution ratio of the fluorescent material is generally obtained. However, when the reference array 7 is calibrated beforehand with the reference array 4 for use in the first embodiment and $I_{Mk}$ is obtained, an absolute quantity of the fluorescent material can also be obtained.

In the second embodiment, the substrate for reference having no self fluorescent action is preferably used. This is because the reference array 7 cannot secure the sampling region for removing the self fluorescent noise. However, the same substrate as that of the reference array 7 is used as a second reference array as such, the region corresponding to each probe array element is used as the sampling region, the self luminescent intensity is detected, and the intensity is subtracted from the signal intensity $P_{Mk}$. Thereby, even with the substrate for reference having the self fluorescent action, the self fluorescent noise can be removed. In this case, there is an advantage that other noises can also be removed. Moreover, the effect inherent to the second embodiment lies in that the reference array can easily be manufactured. Additionally, the photographing of the reference fluorescent image and the photographing of the sample fluorescent image may be performed in reverse order without any problem similarly as the first embodiment.

According to the present invention, the following actions are produced.

(1) According to the biochemical examination method of the present invention, the sample fluorescent image is corrected with the reference fluorescent image. Therefore, even when the lighting is not uniform, the reaction state of the probe with the biochemical material in each probe array element can accurately be examined.

(2) When the reaction carrier having the solid structure is used, the reaction system becomes complicated, and therefore sometimes become inaccurate. However, according to the biochemical examination method of the present invention, actual comparison can be performed, and the action/effect by the above (1) is enlarged.

(3) According to the biochemical examination method of the present invention, in addition to the action/effect by the above (1), even when the state of the probe held by each probe array element has a difference, the reaction state of the reference sample is compared with that of the sample to be examined, and it is therefore possible to accurately examine the reaction state of the probe for each probe array element with the sample to be examined.

(4) According to the biochemical examination method of the present invention, it is possible to accurately examine the reaction state of the probe for each probe array element with the sample to be examined.

(5) According to the biochemical examination method of the present invention, the reference array can easily be manufactured.

(6) According to the biochemical examination method of the present invention, the excitation light noise in the vicinity of the probe array element can be removed, and it is possible to accurately examine the reaction state in each probe array element.

(7) According to the biochemical examination method of the present invention, when the reaction carrier having the solid structure is used, the optical property in the surface is complicated, therefore the noise in the vicinity of the probe array element can be corrected, and the action/effect by the above (6) is enlarged.

(8) According to the biochemical examination method of the present invention, in addition to the action/effect by the above (6), even when the state of the probe held by each probe array element has a difference, the reaction state of the reference sample is compared with that of the sample to be examined, and it is therefore possible to accurately examine the reaction state of the probe for each probe array element with the sample to be examined.

(9) According to the biochemical examination method of the present invention, the excitation light noise in the vicinity of the array element can be removed, and it is possible to accurately examine the reaction state in each array element.

(10) According to the biochemical examination method of the present invention, when the reaction carrier having the solid structure is used, the reaction amount is proportional to the area of the probe array element, and the pipetting error of the probe is corrected by the area and removed. Therefore, it is possible to accurately compare the reaction states of the probes for the respective probe array elements with the sample to be examined.

(11) According to the biochemical examination method of the present invention, in addition to the action/effect by the above (10), even when the state of the probe held by each probe array element has a difference, the reaction state of the reference sample is compared with that of the sample to be examined, and it is therefore possible to accurately compare the reaction states of the probes for the respective probe array elements and the sample to be examined.

(12) According to the biochemical examination method of the present invention, when the reaction carrier having the solid structure is used, the reaction amount is proportional to the area of the probe array element, and the pipetting error of the probe is corrected by the area and removed. Therefore, it is possible to accurately compare the reaction states of the probes for the respective probe array elements with the sample to be examined.

(13) According to the biochemical examination method of the present invention, in general the fluorescent molecules number in the probe array element is not proportional to the total luminescent intensity, and the total luminescent intensity is given by the bonding equation of the linear coefficient, nonlinear coefficient and coefficient fluorescent molecules number. The nonlinear coefficient is a constant determined by the intermolecular distance, and the structure and reaction condition of the probe array. Moreover, when the nonlinear coefficient is introduced in accordance with the system for use, the number of luminescent molecules present in each probe array element can accurately be obtained.

(14) According to the biochemical examination method of the present invention, when the reaction carrier having the solid structure is used, the reaction system becomes complicated, but the nonlinear coefficient corresponding to the system is used, and the action/effect by the above (13) is enlarged.

(15) According to the biochemical examination method of the present invention, in addition to the action/effect by the above (13), even when the state of the probe held by each probe array element has a difference, the reaction state of the reference sample is compared with that of the sample to be examined, and it is therefore possible to accurately examine the reaction states of the probes for the respective probe array elements and the sample to be examined.

(16) According to the biochemical examination method of the present invention, in general the number of luminescent molecules in the probe array element is not proportional to the total luminescent intensity, and the total luminescent intensity is given by the bonding equation of the linear coefficient, nonlinear coefficient and luminescent molecules number. The nonlinear coefficient is a constant determined by the intermolecular distance, and the structure and reaction condition of the probe array. Moreover, when the nonlinear coefficient is introduced in accordance with the system for use, the number of fluorescent molecules present in each probe array element can accurately be obtained.

(17) According to the biochemical examination method of the present invention, in general the number of luminescent molecules in the probe array element is not proportional to the total luminescent intensity, and the total luminescent intensity is given by the bonding equation of the linear coefficient, nonlinear coefficient and luminescent molecules number. The nonlinear coefficient is a constant determined by the intermolecular distance, and the structure and reaction condition of the probe array. Moreover, when the nonlinear coefficient is introduced in accordance with the system for use, the number of fluorescent molecules present in each probe array element can accurately be obtained.

(18) According to the biochemical examination method of the present invention, in general the number of luminescent molecules in the probe array element is not proportional to the total luminescent intensity, and the total luminescent intensity is given by the bonding equation of the linear coefficient, nonlinear coefficient and luminescent molecules number. The nonlinear coefficient is a constant determined by the intermolecular distance, and the structure and reaction condition of the probe array. Moreover, when the nonlinear coefficient is introduced in accordance with the system for use, the number of fluorescent molecules present in each probe array element can accurately be obtained.

(19) According to the biochemical examination method of the present invention, the number of luminescent molecules for each color present in each probe array element can be obtained.

(20) According to the biochemical examination method of the present invention, in general the number of luminescent molecules in the probe array element is not proportional to the total luminescent intensity, and the total luminescent intensity is given by the bonding equation of the linear coefficient, nonlinear coefficient and luminescent molecules number. The nonlinear coefficient is a constant determined by the intermolecular distance, and the structure and reaction condition of the probe array. Moreover, when the nonlinear coefficient is introduced in accordance with the system for use, the number of fluorescent molecules present in each probe array element can accurately be obtained.

Figure 12:
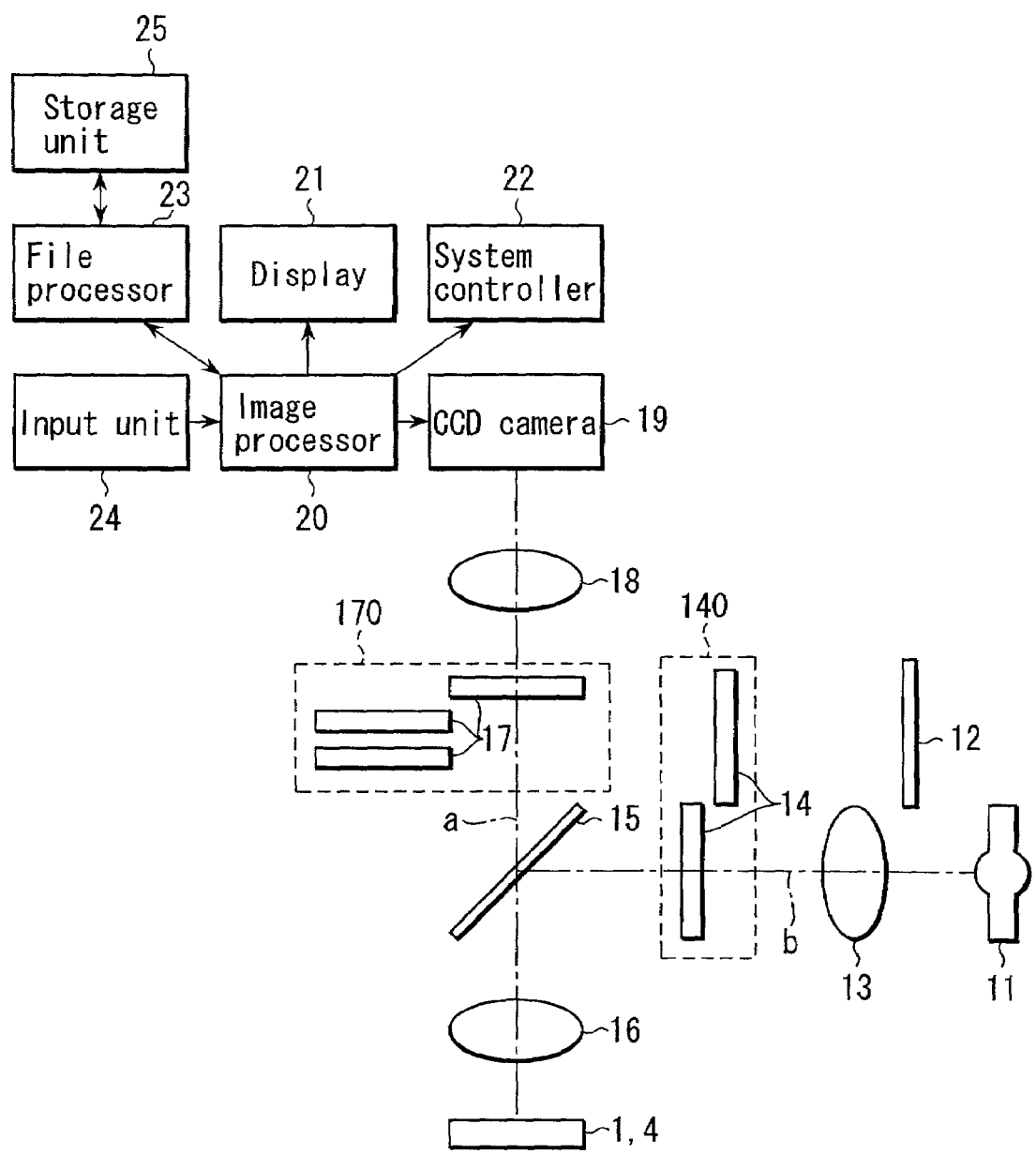
FIG. 12 is a diagram showing the configuration of the microscope apparatus to carry out the biochemical examination method according to a third embodiment of the present invention.

FIG. 12 is a diagram showing the configuration of the microscope apparatus to carry out the biochemical examination method according to a third embodiment of the present invention. In FIG. 12, the same part as that of FIG. 1 is denoted with the same reference numerals.

In FIG. 12, the image processor 20 is connected to a system controller 22, file processor 23, and input unit 24. The file processor 23 is connected to a storage unit 25. The input unit 24 includes a mouse and various buttons. Additionally, the excitation filter 14, dichroic mirror 15, and ND filter 17 configure a cube unit. A foreign particle detection cube, cube for a reference, and cube for a fluorescent light M are configured in accordance with a combination of the excitation filter 14, dichroic mirror 15, and ND filter 17 on the observation light path a and lighting path b.

FIGS. 13 to 21 are flowcharts showing the examination procedure according to the third embodiment. The examination method and action will be described hereinafter with reference to FIGS. 13 to 21.

Figure 13:
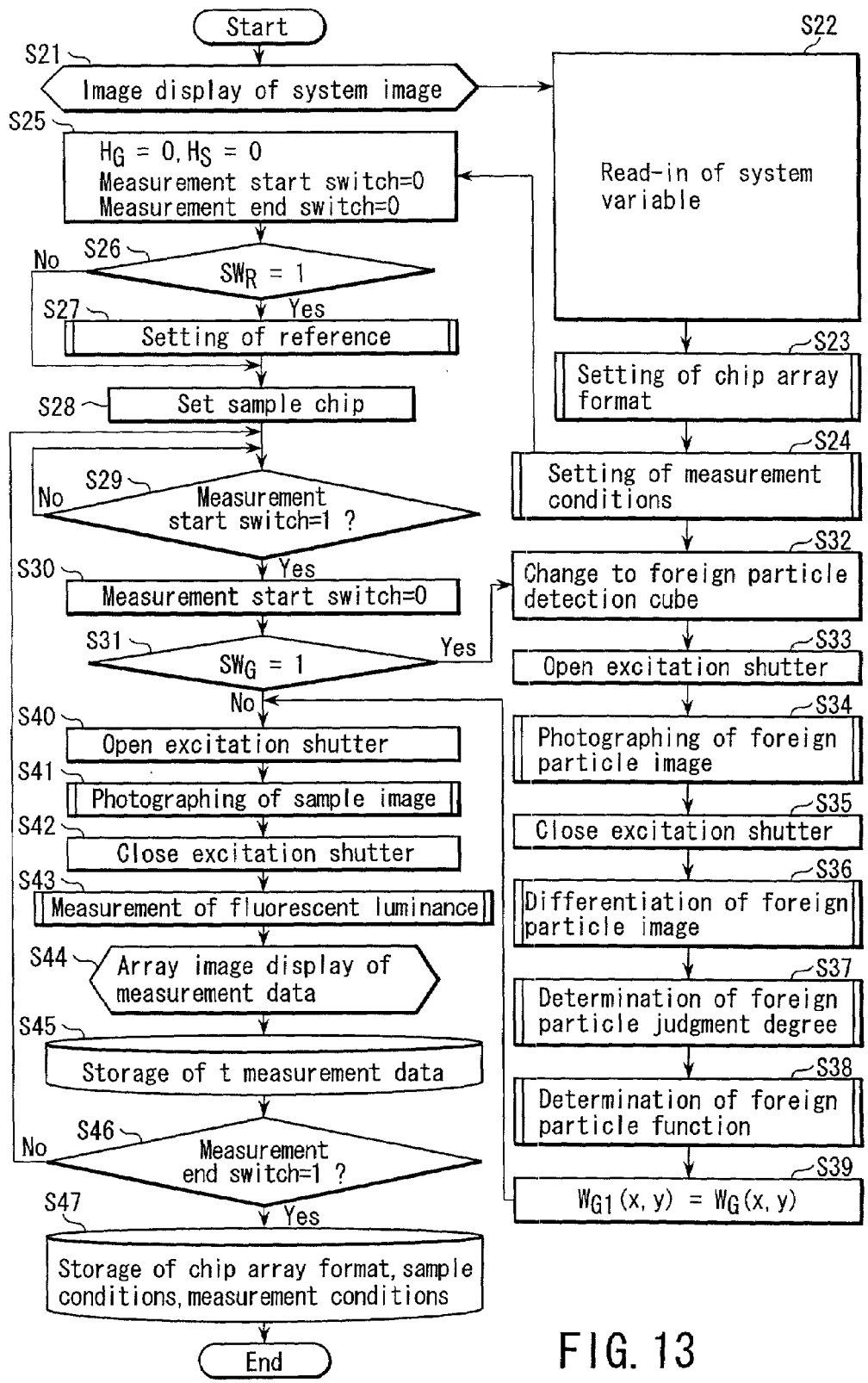

FIG. 13 is a main flowchart showing a procedure of fluorescent luminance measurement. In step S21, a system image is displayed in the display 21. In step S22, the image processor 20 reads system variables from the storage unit 25 via the file processor 23. The system variables are as follows:

$\beta$; lateral magnification of optics, $A_s$; detected numerical aperture, $\Delta$; absolute value of the defocus amount, $\lambda_G$; foreign particle detected wavelength, $N_x$, $N_y$; effective pixel number of a camera, $P_j$; pixel pitch of the camera, B; AD conversion bit number, and $t_0$; minimum accumulated time.

In step S23, the format of the array for biochemical examination 1 is set as a chip array format. In step S24, measurement conditions are set. In step S25, the image processor 20 sets $H_G=0$, $H_S=0$, measurement start switch=0, and measurement end switch=0. When $SW_R=1$ in step S26, the reference is set in step S27, and the examiner sets the array for biochemical examination 1 as a sample chip in step S28. When $SW_R=1$ is not set in the step S26, the array for biochemical examination 1 is set in step S28. With the measurement start switch=1 in step S29, the image processor 20 sets the measurement start switch=0 in step S30.

With $SW_G=1$ in step S31, the system controller 22 changes the cube unit to a foreign particle detection cube in step S32, and opens the shutter 12 on the light path of the excitation light in step S33. In step S34, after the image processor 20 photographs a foreign particle image (dust image) with the CCD camera 19, the system controller 22 closes the shutter 12 in step S35. The image processor 20 differentiates the foreign particle image in step S36, determines a foreign particle judgment degree in step S37, determines a foreign particle function in step S38, and sets $w_{Gt}(x,y)=w_G(x,y)$ in step S39.

After the step S39, or when $SW_G=1$ is not set in the step S31, the system controller 22 opens the shutter 12 in step S40. After the image processor 20 photographs the sample image with the CCD camera 19 in step S41, the system controller 22 closes the shutter 12 in step S42.

The image processor 20 measures the fluorescent luminance in step S43, displays an array image of measurement data in the display 21 in step S44, and stores t measurement data into the storage unit 25 via the file processor 23 in step S45. Additionally, the measurement data includes $\rho_R$; reference foreign particle percentage, $\rho$; sample foreign particle percentage, $\Gamma_{MB}$; fluorescent background luminance, (i, j); spot address, $\Gamma'''_M(i, j)$; spot luminance, $\Gamma_{MC}(i, j)$; fluorescent crosstalk luminance, $S_M(i, j)$; spot area, and $REM_M(i, j)$; message.

With the measurement end switch=1 in step S46, in step S47 the file processor 23 stores a file with a chip array format, sample conditions, and measurement conditions described therein in the storage unit 25, and ends the processing. When the measurement end switch=1 is not set in the step S46, the processing of and after the step S29 is performed.

Figure 14:
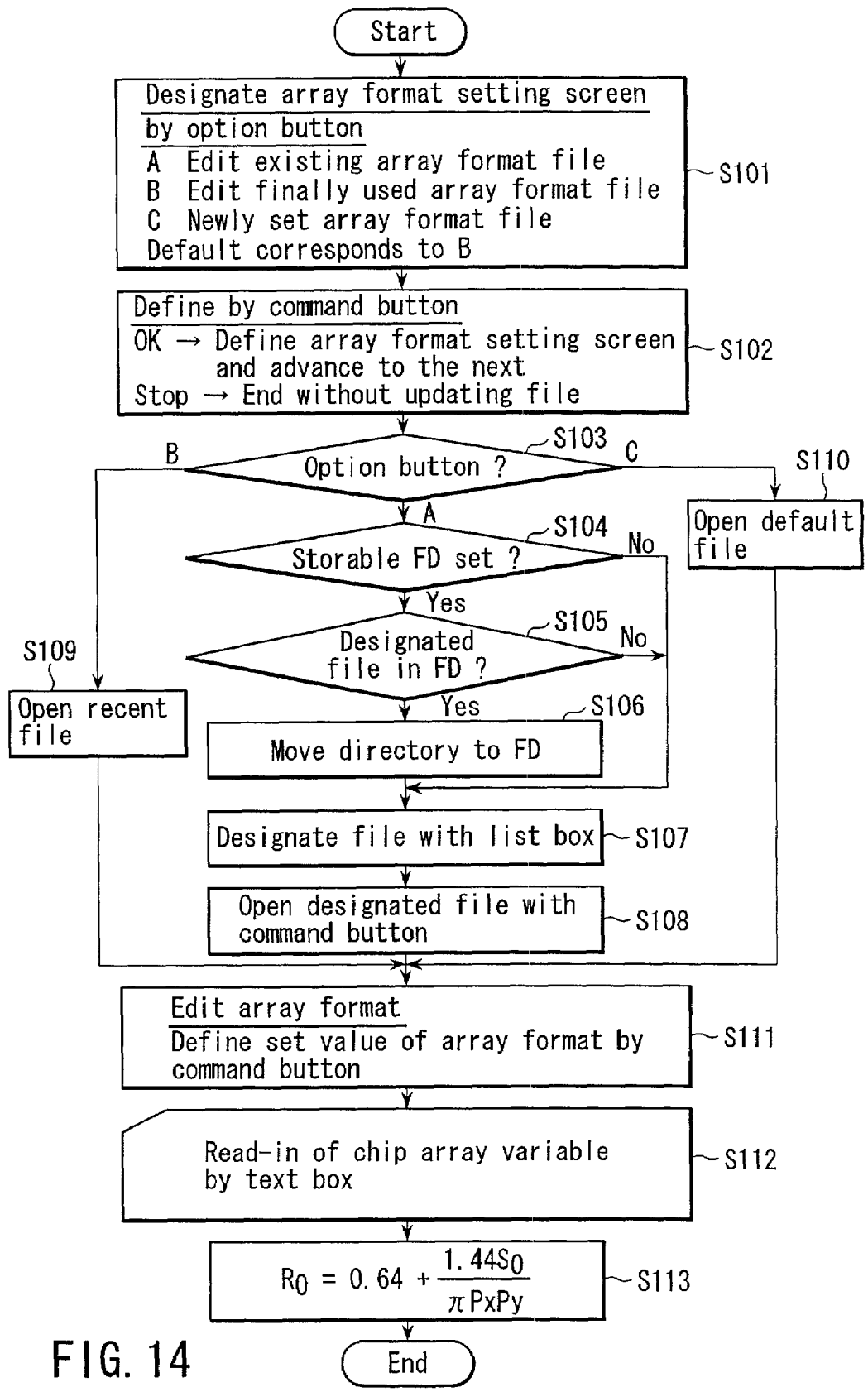

FIG. 14 is a sub flowchart showing a procedure of chip array format setting shown in the step S23. In step S101, the examiner designates an array format setting screen with an option button of the input unit 24. Additionally, option button 'A' indicates "the existing array format file is edited", 'B' indicates "the finally used array format file is edited", 'C' indicates "the array format file is newly set", and default corresponds to 'B'.

In step S102, the examiner defines a command by a command button of the input unit 24. Additionally, command button 'OK' indicates "an array format setting screen is defined and the step advances to the next", and 'stop' indicates "the steps are ended without updating a file".

Option button 'A' is set in step S103, storable floppy disk (FD) is set in step S104, and there is a designated file in the FD in step S105. In this case, in step S106, the file processor 23 moves a directory to the FD. The examiner designates the file by a list box via the input unit 24 in step S107, and opens the designated file by the command button in step S108.

When option button 'B' is set in the step S103, the file processor 23 opens a recent file stored in the storage unit 25 in step S109. When option button 'C' is set in the step S103, the file processor 23 opens a default file in step S110. After steps S108, S109, S110, the examiner defines a set value of an array format by the command button of the input unit 24 in step S111.

In step S112, the image processor 20 reads chip array variables defined by the text box in the step S111. The chip array variables are as follows:

$S_0$; standard area per probe, $P_x$, $P_y$; pitch of the probe, $m_x$, $m_y$; probe arrangement number, and $N_P$; the number of probes for position detection.

In step S113, the image processor 20 calculates $R_0=0.64+1.44S_0/\pi P_x P_y$, and ends the processing.

Figure 15:
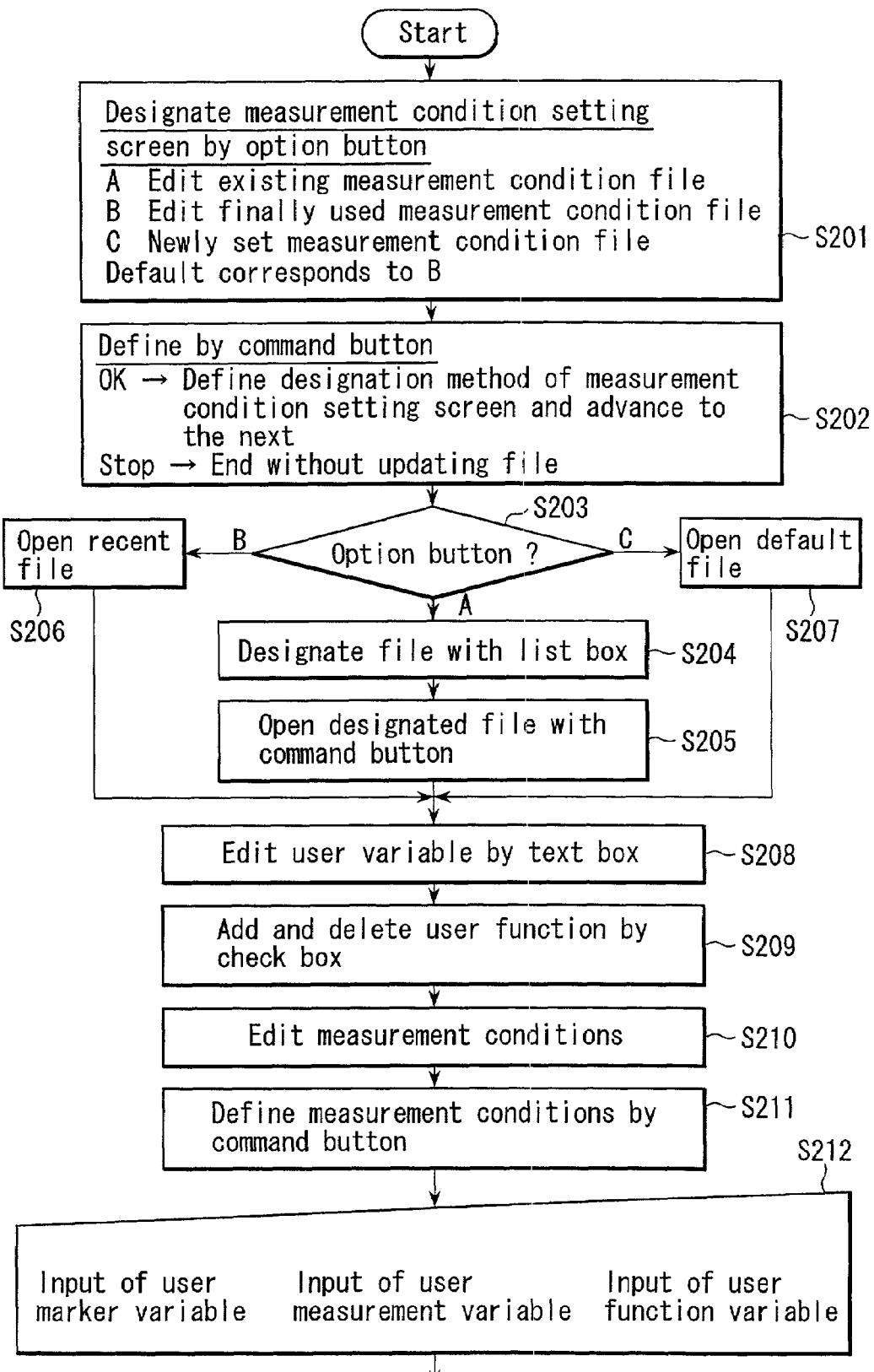

FIG. 15 is a sub flowchart showing the procedure of the measurement condition setting shown in the step S24. In step S201, the examiner designates a measurement condition setting screen by the option button of the input unit 24. Additionally, the option button 'A' indicates "the existing measurement condition file is edited", 'B' indicates "the finally used measurement condition file is edited", 'C' indicates "the measurement condition file is newly set", and the default corresponds to 'B'.

In step S202, the examiner defines the command by the command button of the input unit 24. Additionally, command button 'OK' indicates "a designation method of the measurement condition setting screen is defined and the step advances to the next", and 'stop' indicates "the steps are ended without updating the file".

When the option button 'A' is set in step S203, the examiner designates the file by the list box via the input unit 24 in step S204, and opens the designated file by the command button in step S205. When the option button 'B' is set in step S203, the file processor 23 opens the recent file stored in the storage unit 25 in step S206. When option button 'C' is set in the step S203, the file processor 23 opens the default file stored in the storage unit 25 in step S207.

After the steps S205, S206, S207, the examiner edits user variables by the text box in the input unit 24 in step S208. In step S209, the examiner adds or deletes a user function by a check box in the input unit 24. In step S210, the examiner edits the measurement conditions in the input unit 24. In step S211, the examiner defines the measurement conditions by the command button of the input unit 24.

In step S212, the image processor 20 reads user marker variables, user measurement variables, and user function variables defined in the step S211 from the input unit 24, and the image processor 20 ends the processing.

The user marker variables are as follows (a value in ( ) indicates a default value):

$M_{max}$; fluorescent marker number (2), $M_A$; fluorescent marker of sample A (FITC) ($\lambda_A$ automatic input), and $M_B$; fluorescent marker of sample B (TEXS RED) ($\lambda_B$ automatic input) (during $M_{max}=2$).

The user measurement variables are as follows (the value in ( ) indicates the default value):

$t_0$; minimum accumulated time ($t_0$), $n_{max}$; accumulated class number (AUTO), $k_{max}$; measurement number (10), and $N_p$; the number of markers for position detection (the number of probes for position detection) (0).

The user function variables are as follows (1 indicates that the function is attached, 0 indicates that there is no function, and the value in ( ) is the default value):

$SW_R$; reference processing (1), $SW_{RG}$; foreign particle processing of a reference chip (1) (during $SW_R=1$), $SW_B$; background processing (1), $SW_G$; foreign particle processing of the sample (1) (option button is also used), (when non-processed data is also outputted, $SW_G=2$).

Figure 16:
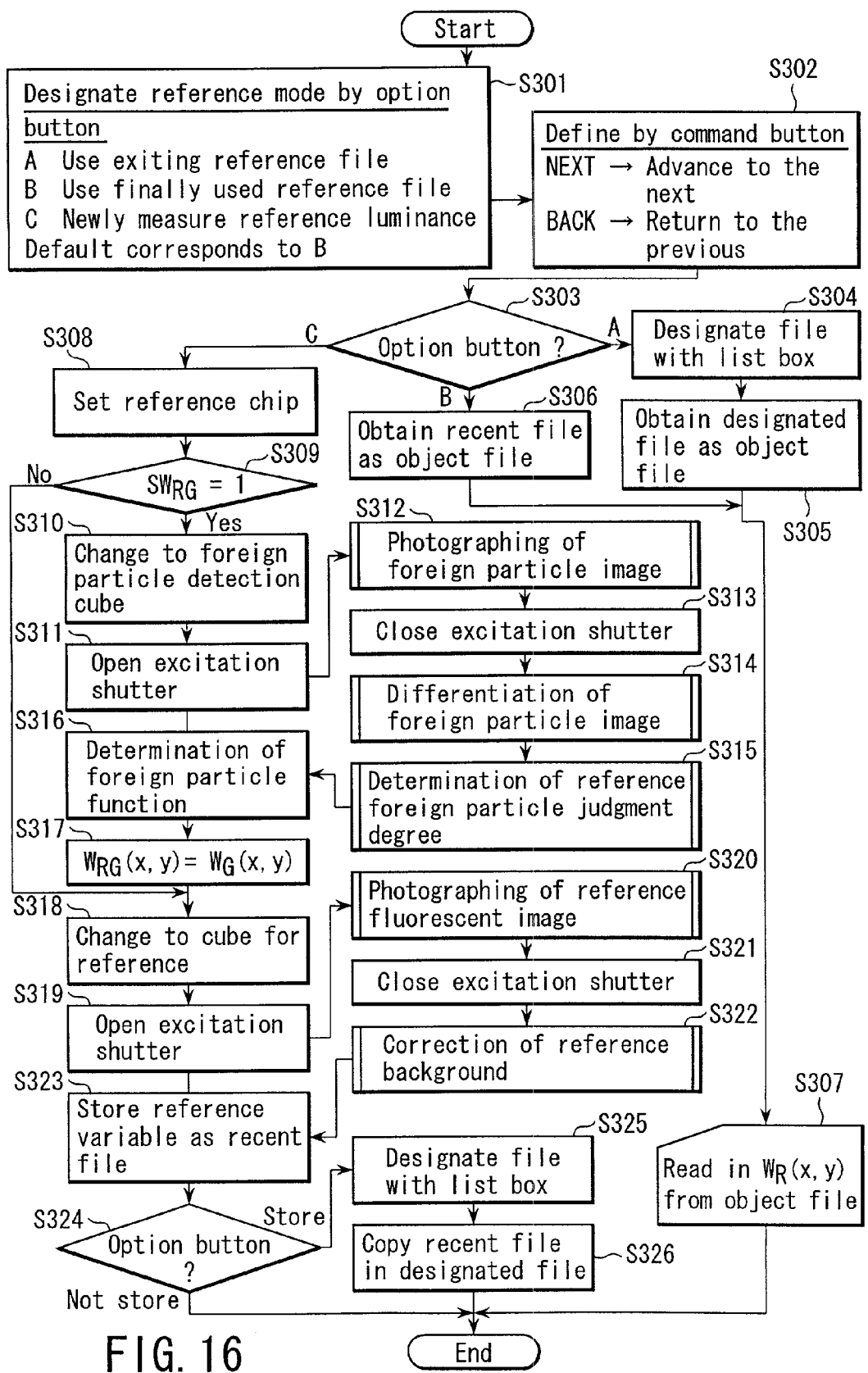

FIG. 16 is a sub flowchart showing the procedure of a reference setting shown in the step S27. In step S301, the examiner designates a reference mode by the option button of the input unit 24. Additionally, the option button 'A' indicates "the existing reference file is used", 'B' indicates "the finally used reference file is used", 'C' indicates "a reference luminance is newly measured", and the default corresponds to 'B'.

In step S302, the examiner defines the command by the command button of the input unit 24. Additionally, command button 'NEXT' indicates "the step advances to the next", and 'BACK' indicates "the step returns".

When the option button 'A' is set in step S303, the examiner designates the file by the list box via the input unit 24 in step S304, and the image processor 20 obtains the designated file as an object file in step S305. When the option button 'B' is set in step S303, the image processor 20 obtains the recent file as the object fine in step S306. After the step S305 or S306, the image processor 20 reads $W_R(x, y)$ from the object file in step S307, and ends the processing.

When the option button 'C' is set in step S303, the examiner sets the reference array 4 as the reference chip in step S308. With $SW_{RG}=1$ in step S309, the system controller 22 changes the cube unit to a foreign particle detection cube in step S310, and opens the shutter 12 in step S311. After the image processor 20 photographs a foreign particle image via the CCD camera 19 in step S312, the system controller 22 closes the shutter 12 in step S313. The image processor 20 differentiates the foreign particle image in step S314, determines a reference foreign particle judgment degree in step S315, determines a foreign particle function in step S316, and sets $w_{RG}(x, y)=W_G(X, y)$ in step S317.

After the step S317, or when $SW_G=1$ is not set in the step S309, the system controller 22 changes the cube unit to the cube for the reference in step S318, and opens the shutter 12 in step S319. After the image processor 20 photographs the reference fluorescent image via the CCD camera 19 in step S320, the system controller 22 closes the shutter 12 in step S321.

The image processor 20 corrects a reference background in step S322, and the file processor 23 stores the reference variable as the recent file in step S323.

When the examiner designates 'store' by the option button of the input unit 24 in step S324, the examiner designates the file by the list box via the input unit 24 in step S325, the file processor 23 copies the recent file in the designated file in step S326, and the processing ends. When the examiner designates 'not store' by the option button of the input unit 24 in the step S324, the image processor 20 ends the processing.

Figure 17:
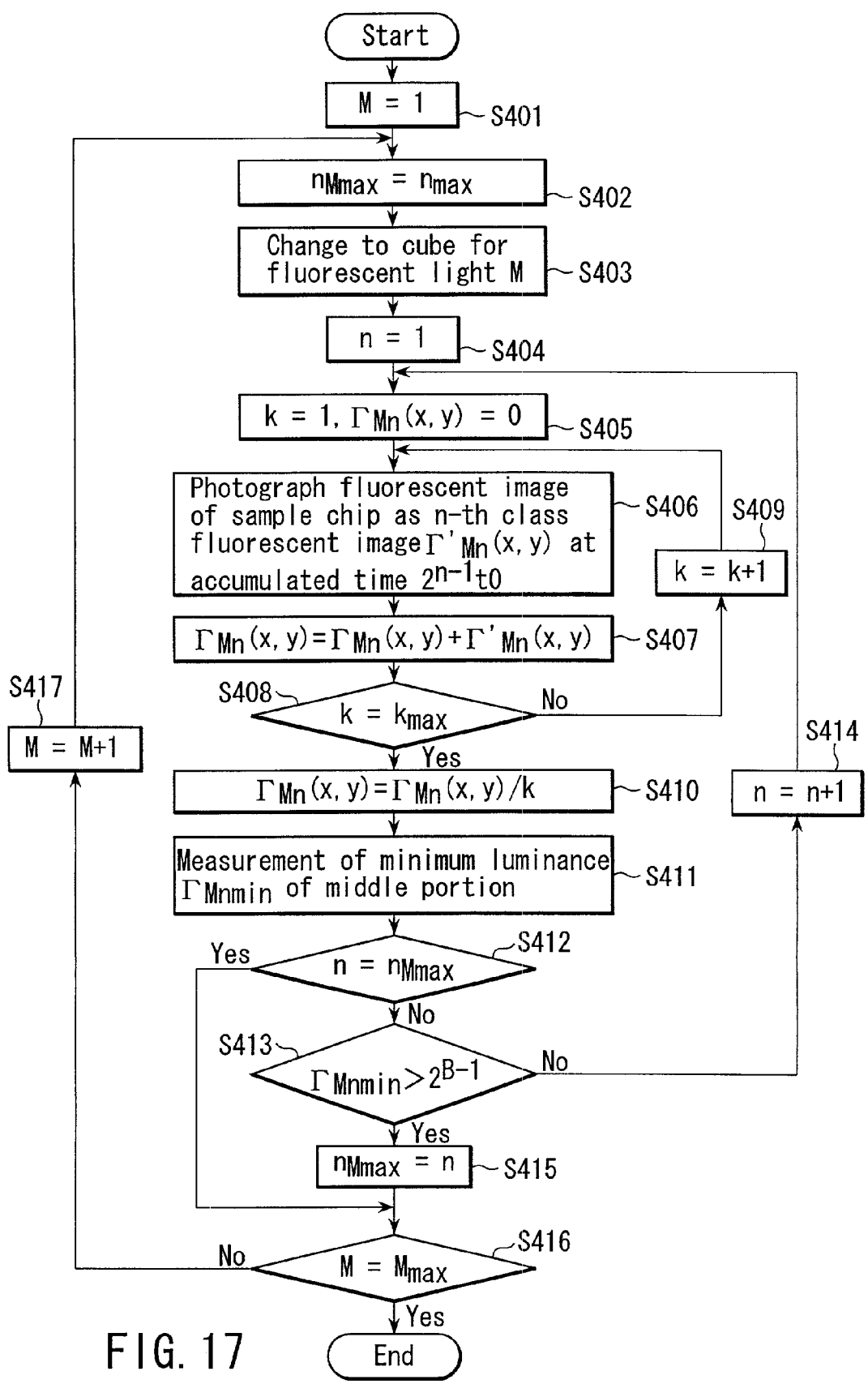

FIG. 17 is a sub flowchart showing a procedure for photographing the sample image shown in the step S41. The image processor 20 sets $M=1$ in step S401, and sets $n_{Mmax}=n_{max}$ in step S402. The examiner changes the cube unit to a cube for the fluorescent light M in step S403. The image processor 20 sets $n=1$ in step S404, and sets $k=1$, $\Gamma_{Mn}(x, y)=0$ in step S405.

The system controller 22 and image processor 20 photograph the fluorescent image of the sample chip as n-th class fluorescent image $\Gamma'_{Mn}(x, y)$ at an accumulated time $2^{n-1}t_0$ with the CCD camera 19 in step S406, and calculates $\Gamma_{Mn}(x, y)=\Gamma_{Mn}(x, y)+\Gamma'_{Mn}(x, y)$ in step S407. When $k=k_{max}$ is not set in step S408, the image processor 20 sets $k=k+1$ in step S409, and performs the processing of and after step S406.

With $k=k_{max}$ in the step S408, the image processor 20 calculates an average image of $k_{max}$ images by $\Gamma_{Mn}(x, y)=\Gamma_{Mn}(x, y)/k$ in step S410, and measures a minimum luminance $\Gamma_{Mnmin}$ of an image middle portion in step S411.

In this manner, a plurality of fluorescent images of the sample chip having the same accumulated time are photographed, and the average image of these fluorescent images is calculated.

When $n=n_{Mmax}$ is not set in step S412, and $\Gamma_{Mnmin}>2^{B-1}$ is not set in step S413, the image processor 20 sets $n=n+1$ in step S414, and performs the processing of and after step S405. With $\Gamma_{Mnmin}>2^{B-1}$ in the step S413, the image processor 20 sets $n_{Mmax}=n$ in step S415.

After the step S415, or when $n=M_{max}$ is set in the step S412, and when $M=M_{max}$ is not set in step S416, the image processor 20 sets $M=M+1$ in step S417, and performs the processing of and after the step S402. With $M=M_{max}$ in the step S416, the image processor ends the processing.

Figure 18:
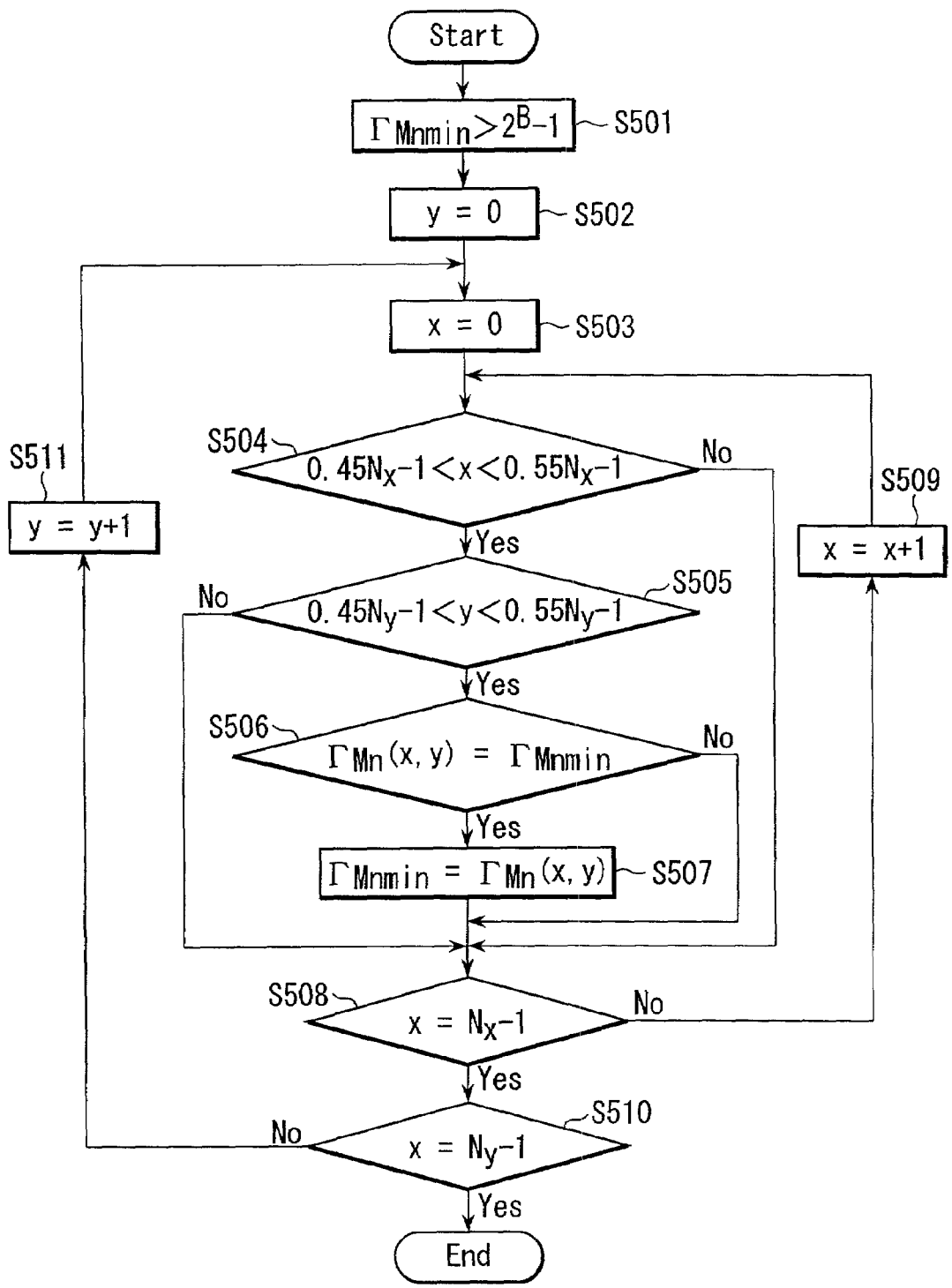

FIG. 18 is a sub flowchart showing a procedure for measuring the minimum luminance of the middle portion shown in the step S411. The image processor 20 sets $\Gamma_{Mnmin}=2^B-1$ in step S501, sets $y=0$ in step S502, and sets $x=0$ in step S503. When $0.45N_x-1<x<0.55N_x-1$ in step S504, $0.45N_y-1<y<0.55N_y-1$ in step S505, and $\Gamma_{Mn}(x, y)<\Gamma_{Mnmin}$ in step S506, the image processor 20 sets $\Gamma_{Mnmin}=\Gamma_{Mn}(x, y)$ in step S507.

After the step S507, when $0.45N_x-1<x<0.55N_x-1$ is not set in the step S504, when $0.45N_y-1<y<0.55N_y-1$ is not set in step the S505, or when $\Gamma_{Mn}(x, y)<\Gamma_{Mnmin}$ is not set in the step S506, and when $x=N_x-1$ is not set in step S508, the image processor 20 sets $x=x+1$ in step S509, and performs the processing of and after the step S504.

When $x=N_x-1$ is set in the step S508, and $y=N_y-1$ is not set in step S510, the image processor 20 sets $y=y+1$ in step S511, and performs the processing of and after the step S503. When $y=N_y-1$ is set in the step S510, the image processor 20 ends the processing.

Figure 19:
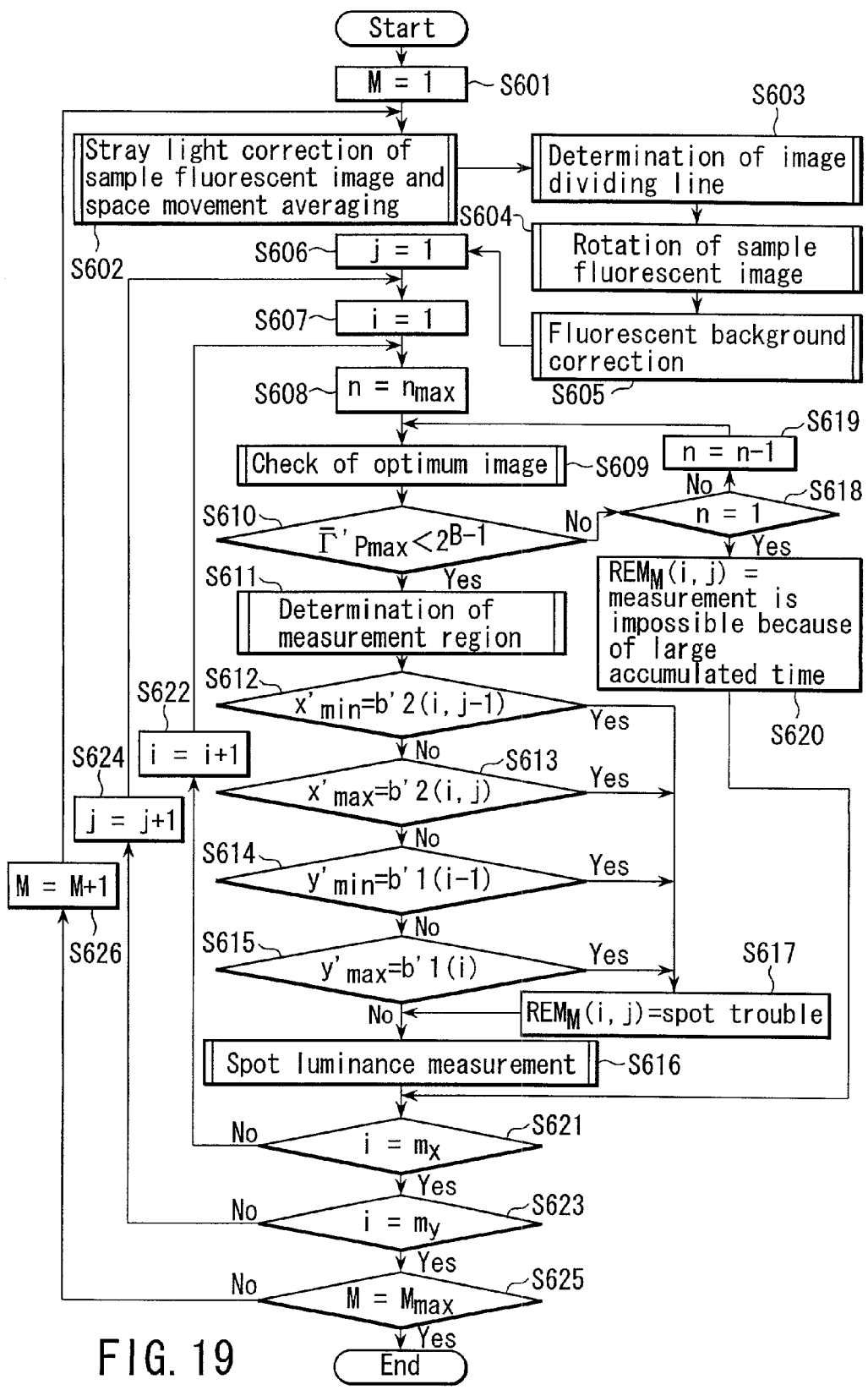

FIG. 19 is a sub flowchart showing the procedure for measuring the fluorescent luminance shown in the step S43. The image processor 20 sets M=1 in step S601, and performs stray light correction and space movement averaging processing of the sample fluorescent image in step S602. The image processor 20 determines an image dividing line in step S603, rotates the sample fluorescent image in step S604, and performs fluorescent background correction in step S605. In the fluorescent background correction, a minimum detected amount of the fluorescent light in the noise sampling region (local background region) of the sample fluorescent image is used as a fluorescent background, and the fluorescent image obtained by subtracting the fluorescent background from the sample fluorescent image is used as the object image. In this case, as shown in FIG. 4, a boundary of the measurement region 42 is set to be the same as a boundary of the noise sampling region 43.

The image processor 20 sets j=1 in step S606, i=1 in step S607, and n=$n_{max}$ in step S608. The image processor 20 checks an optimum image in step S609, and determines the measurement region in step S611, when the following is set in step S610.

$$\Gamma'_{P\,max} < 2^{B-1}$$

When $x'_{min}=b_2'(i,j-1)$ is not set in step S612, $x'_{max}=b_2'(i,j)$ is not set in step S613, $y'_{min}=b_1'(i-1)$ is not set in step S614, and $y'_{max}=b_1'(i)$ is not set in step S615, the image processor 20 measures a spot luminance in step S616. When $x'_{min}=b_2'(i,j-1)$ is set in the step S612, $x'_{max}=b_2'(i,j)$ is set in the step S613, $y_{min}=b_1'(i-1)$ is set in the step S614, or $y'_{max}=b_1'(i)$ is set in the step S615, the image processor 20 sets $REM_M(i,j)$=spot trouble in step S617.

When the following is not set in the step S610, and n=1 is not set in step S618, the image processor 20 sets n=n−1 in step S619, and performs of and after the step S609.

$$\Gamma'_{P\,max} < 2^{B-1}$$

When n=1 in the step S618, the image processor 20 sets $REM_M(i,j)$=measurement is impossible because of a large accumulated time in step S620.

After the step S616 or the step S620, and when I=$m_x$ is not set in step S621, the image processor 20 sets i=i+1 in step S622, and performs the processing of and after the step S608. When i=$m_x$ is set in the step S621, and j=$m_y$ is not set in step S623, the image processor 20 sets j=j+1 in step S624, and performs the processing of and after the step S607. When j=$m_y$ is set in the step S623, and M=$M_{max}$ is not set in step S625, the image processor 20 sets M=M+1 in step S626, and performs the processing of and after the step S602. When M=$M_{max}$ in the step S625, the image processor 20 ends the processing.

Additionally, the sample fluorescent image is subjected to a smoothing processing by the space movement averaging in the step S602, but the smoothing processing may be performed using an averaging operator.

Figure 20:
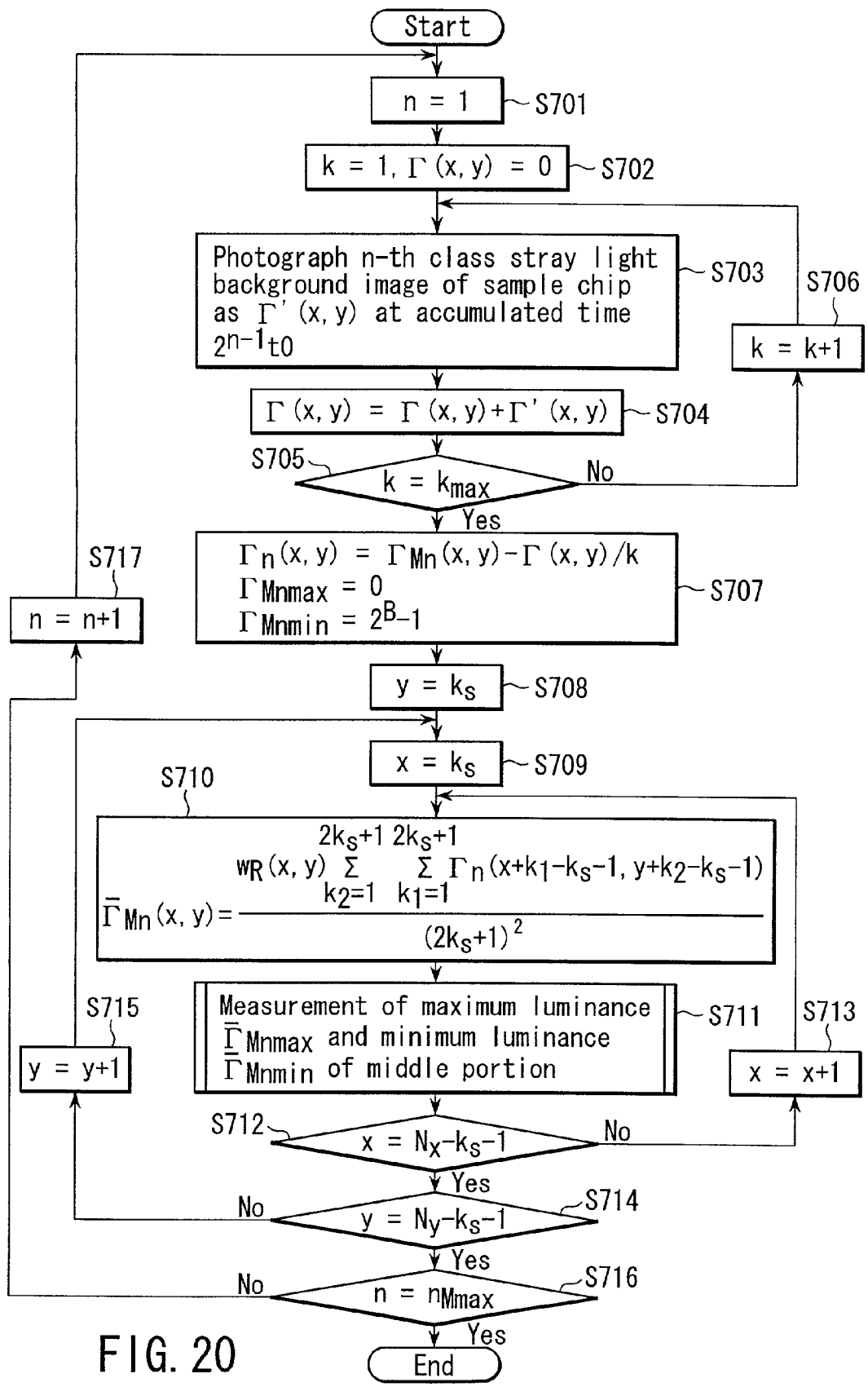

FIG. 20 is a sub flowchart showing a procedure for the stray light correction and space movement averaging of the sample fluorescent image shown in the step S602. The image processor 20 sets n=1 in step S701, and sets k=1, $\Gamma(x, y)=0$ in step S702. The image processor 20 photographs an n-th class stray light background image of the sample chip as $\Gamma''(x, y)$ at the accumulated time $2^{n-1}t_0$ via the CCD camera 19 in step S703, and sets $\Gamma(x, y)=\Gamma(x, y)+\Gamma''(x, y)$ in step S704.

When k=$k_{max}$ is not set in step S705, the image processor 20 sets k=k+1 in step S706, and performs the processing of and after the step S703. When k=$k_{max}$ is set in the step S705, the image processor 20 calculates the average image of $k_{max}$ images by $\Gamma_n(x, y)=\Gamma_{Mn}(x, y)-\Gamma(x, y)/k$, and sets $\Gamma_{Mnmax}=0$, $\Gamma_{Mnmin}=2^B-1$ in step S707. The image processor 20 sets y=$k_s$ in step S708, and x=$k_s$ in step S709.

The image processor 20 calculates the following in step S710.

$$\Gamma_{Mn}(x,y) = \frac{w_R(x,y)\sum_{k_2=1}^{2k_s+1}\sum_{k_1=1}^{2k_s+1}\Gamma_n(x+k_1-k_s-1, y+k_2-k_2-1)}{(2k_s+1)^2}$$

The processor measures the maximum luminance of the image middle portion in step S711 as follows.

$$\Gamma_{Mn\,max}$$

Moreover, the processor measures the minimum luminance as follows.

$$\Gamma_{Mn\,min}$$

When x=$N_x-k_s-1$ is not set in step S712, the image processor 20 sets x=x+1 in step S713, and performs the processing of and after the step S710. When x=$N_x-k_s-1$ is set in the step S712, and y=$N_y-k_s-1$ is not set in step S714, the image processor 20 sets y=y+1 in step S715, and performs the processing of and after the step S709. When y=$N_y-k_s-1$ is set in the step S714, and n=$n_{Mmax}$ is not set in step S716, the image processor 20 sets n=n+1 in step S717, and performs the processing of and after the step S702. When n=$n_{Mmax}$ in the step S716, the image processor 20 ends the processing.

Figure 21A:
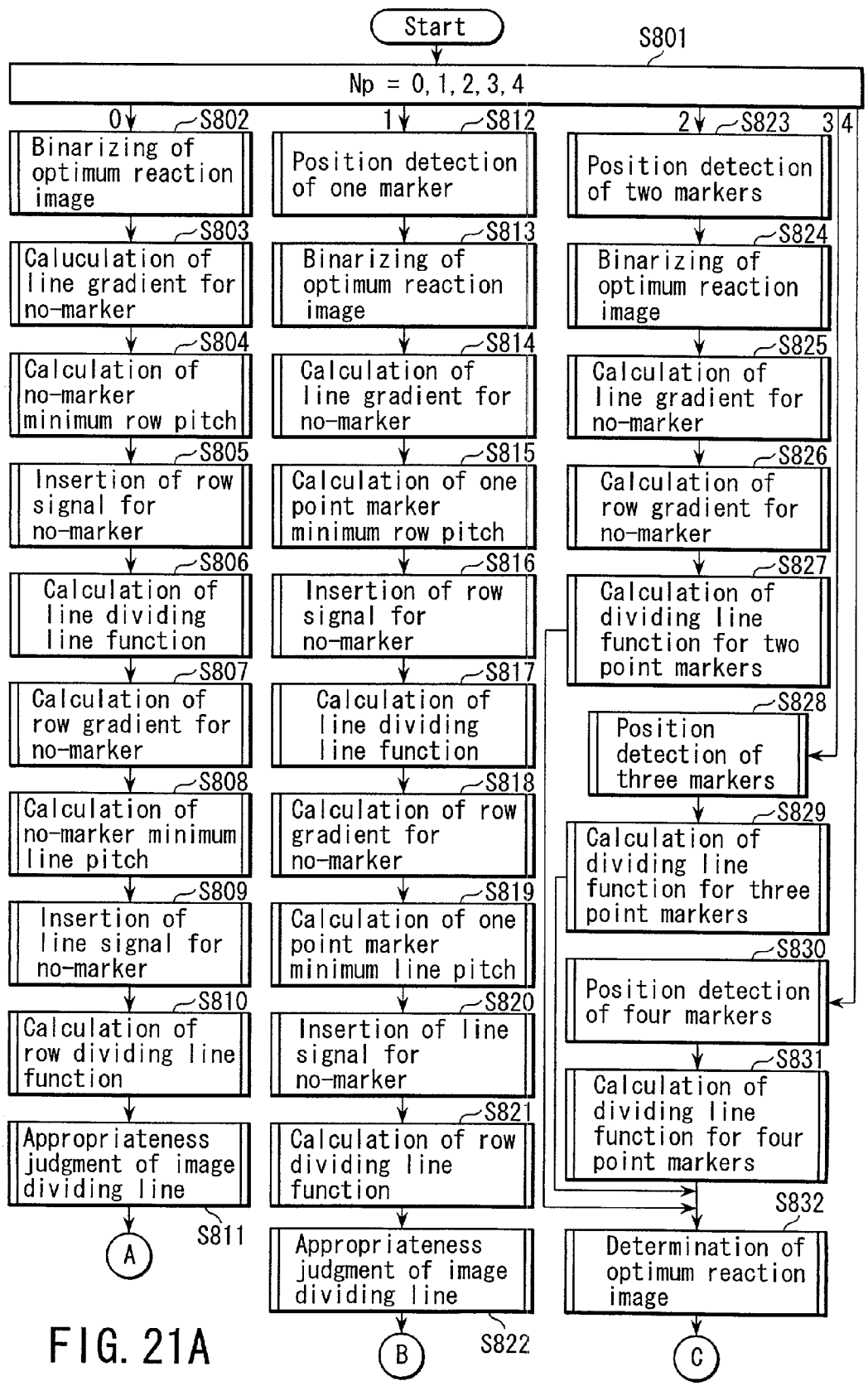
Figure 21B:
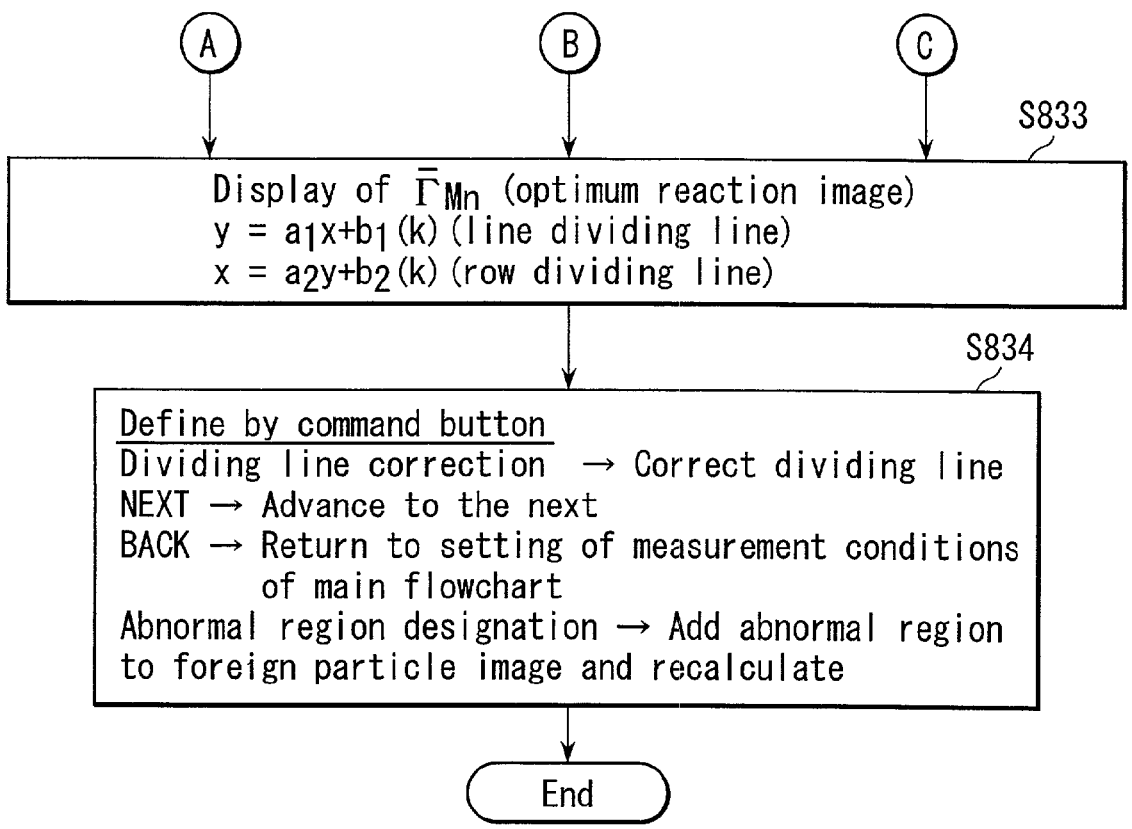

FIGS. 21A and 21B are sub flowcharts showing a procedure for determining an image dividing line shown in the step S603. When the number of markers for position detection (the number of probes for position detection) is $N_P$=0 in step S801, the image processor 20 binarizes an optimum reaction image (whole image) in step S802, calculates a line gradient for no marker in step S803, calculates a no-marker minimum row pitch in step S804, inserts a row signal for no marker in step S805, and calculates a line dividing line function in step S806 with respect to the binarized whole image.

Furthermore, the image processor 20 calculates a row gradient for no marker in step S807, calculates a no-marker minimum line pitch in step S808, inserts a line signal for no marker in step S809, and calculates a row dividing line function in step S810 with respect to the whole image of the binarized sample fluorescent image. The image processor 20 judges whether or not the obtained image dividing line is appropriate in step S811.

When $N_P$=1 in the step S801, the image processor 20 detects the position of one marker in step S812, binarizes the optimum reaction image (whole image) in step S813, calculates the line gradient for no marker in step S814, calculates a one-point marker minimum row pitch in step S815, inserts a row signal for no marker in step S816, and calculates a line dividing line function in step S817.

Furthermore, the image processor 20 calculates the row gradient for no marker in step S818, calculates a one point marker minimum line pitch in step S819, inserts the line signal for no marker in step S820, and calculates the row dividing line function in step S821 with respect to binarized whole image. The image processor 20 judges whether or not the obtained image dividing line is appropriate in step S822.

When $N_P=2$ in the step S801, the image processor 20 detects the positions of two markers in step S823, binarizes the optimum reaction image (whole image) in step S824, calculates the line gradient for no marker in step S825, calculates the row gradient for no marker in step S826, and calculates a dividing line function for two-point markers in step S827 with respect to the binarized whole image. The image processor 20 determines the optimum reaction image in step S832.

When $N_P=3$ in the step S801, the image processor 20 detects the positions of three markers in step S828, calculates the dividing line function for three-points markers in step S829, and determines the optimum reaction image in the step S832. When $N_P=4$ in the step S801, the image processor 20 detects the positions of four markers in step S830, calculates the dividing line function for four-points markers in step S831, and determines the optimum reaction image in the step S832.

After the step S811, S822 or S832, the image processor 20 displays the following image and lines indicated, $\Gamma_{Mn}$(optimum reaction image), $y=a_1x+b_1(k)$ (line dividing line), and $x=a_2y+b_2(k)$ (row dividing line) in the display 21.

Figure 22:
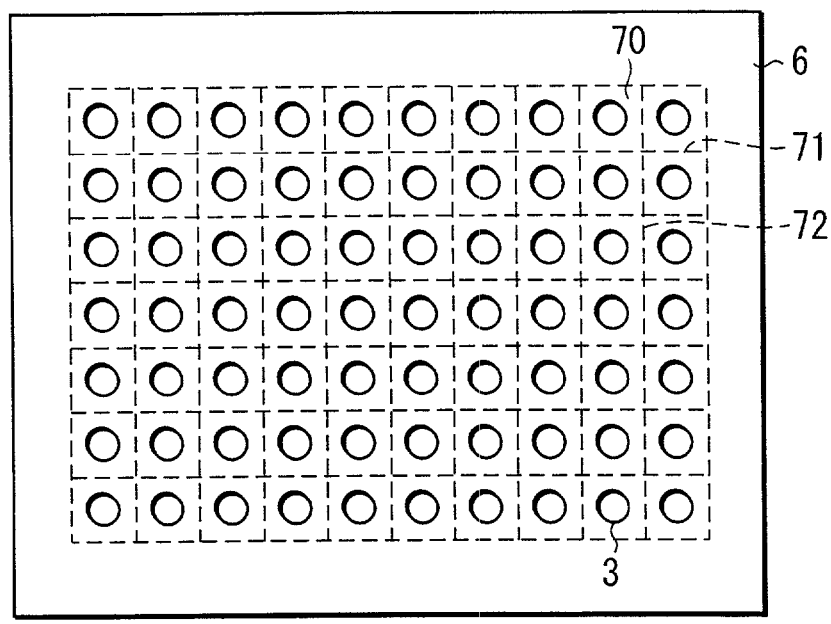
FIGS. 22, 23 are schematic diagrams showing a dividing line displayed on the sample fluorescent image according to the third embodiment of the present invention.

FIG. 22 is a schematic diagram showing the dividing line displayed on the sample fluorescent image in the display 21. FIG. 22 shows that the number of markers for position detection (the number of probes for position detection) is $N_P=0$. As shown in FIG. 22, the image processor 20 divides the sample fluorescent image into a plurality of divided images 70 by a probe array element unit by a plurality of line dividing lines 71 (lateral broken lines) and row dividing lines 72 (vertical broken lines). In this case, each divided image 70 forms a substantially square shape. The examiner designates the measurement region and noise sampling region (local background region) on each divided image 70 of the sample fluorescent image displayed in an enlarged size in the display 21 by a mouse or the like of the input unit 24. The image processor 20 detects the local background from the noise sampling region, and uses this detected amount to correct the detected amount from the measurement region.

In step S834, the examiner defines the command with the command button of the input unit 24. Additionally, command button 'dividing line correction' indicates "to correct the dividing line", 'NEXT' indicates "the step advances to the next", 'BACK' indicates "the step returns to the setting of the measurement conditions of the main flowchart (step S24)", and 'abnormal region designation' indicates "an abnormal region is added to a foreign particle image and calculated again".

When 'abnormal region designation' is defined, the examiner designates the abnormal region on the sample fluorescent image displayed in the display 21 with the mouse or the like of the input unit 24. The abnormal region is regarded abnormal, but the region is not processed as the foreign particle image. The image processor 20 regards the designated abnormal region as a region outside the examination object. Furthermore, the image processor 20 adds the region of the foreign particle image to the abnormal region, and forms the region outside the examination object.

Figure 23:
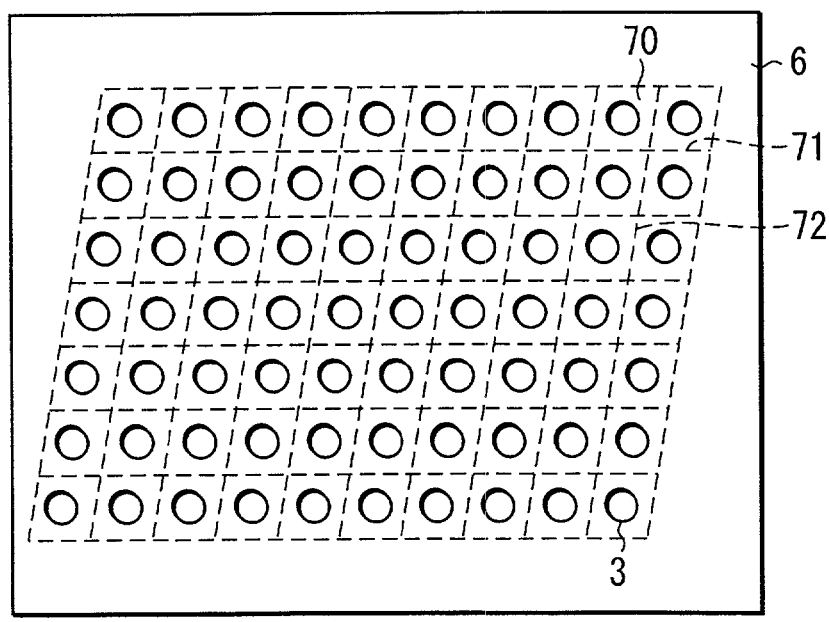

FIG. 23 is a concept diagram showing the dividing line displayed on the sample fluorescent image of the display 21. FIG. 23 shows that the number of markers for position detection (the number of probes for position detection) is $N_P=0$. As shown in FIG. 23, the image processor 20 divides the sample fluorescent image into a plurality of divided images 70 by the probe array element unit by the plurality of line dividing lines 71 and row dividing lines 72. In this case, each divided image 70 forms a parallelogram.

As shown in FIG. 23, the arrangement state of the probe array elements 3 in the array for biochemical examination continuously deviates in each line (in each row, or in each of the lines and rows), and sometimes has a gradient in each row (in each line, or in each of the lines and rows). In this case, the image is divided as shown in FIG. 22, and the divided image of each probe array element 3 cannot be formed substantially in the square shape. Therefore, the image processor 20 performs a processing of inclining at least one of all the line dividing lines 71 and all the row dividing lines 72 (all the row dividing lines 72 in FIG. 23) by a predetermined angle in accordance with the arrangement state of the probe array elements 3. Thereby, each divided image of the probe array element 3 forms the parallelogram.

Figure 24:
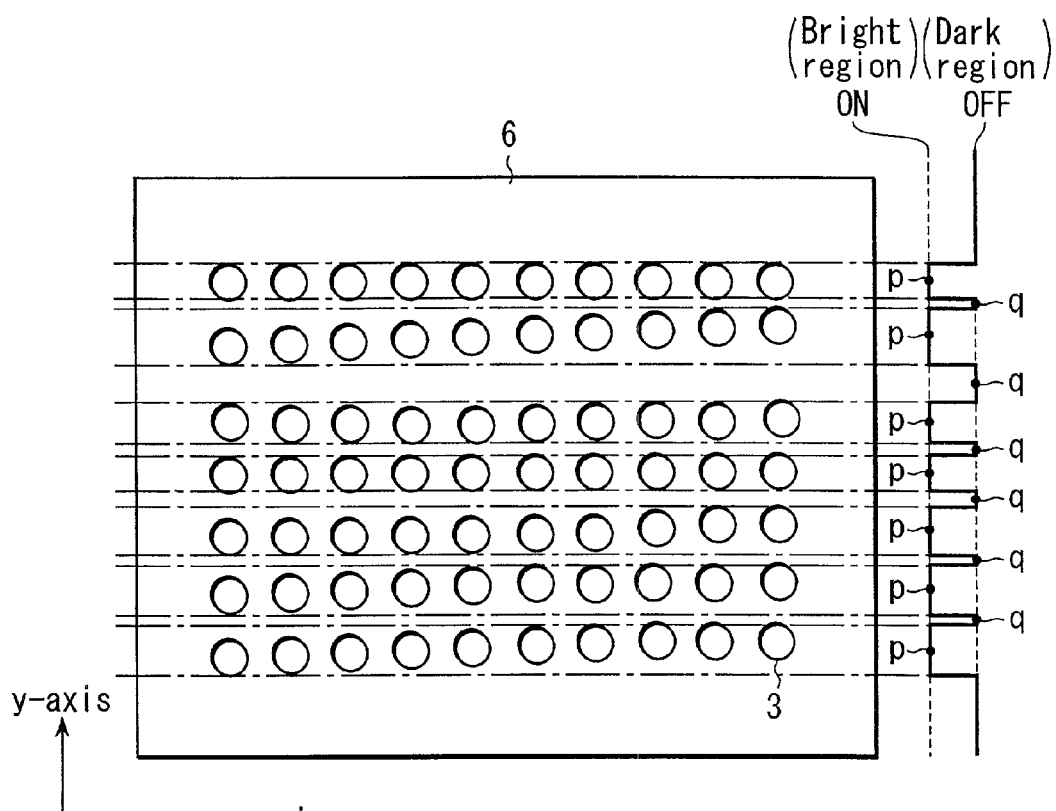
FIG. 24 is a schematic diagram showing a gradient calculation example of a line dividing line and row dividing line according to the third embodiment of the present invention.

FIG. 24 is a schematic diagram showing a gradient calculation example of the line dividing line and row dividing line of the binarized sample fluorescent image. FIG. 24 shows that the number of markers for position detection (the number of probes for position detection) is $N_P=0$. In FIG. 24, it is assumed that the portion of each probe array element 3 in the whole image is a bright region, and the other portion is a dark region in the formed binarized image. Additionally, the image processor 20 binarizes the sample fluorescent image with the middle value of the output value in the measurement region, and obtains the binarized image.

The image processor 20 detects the bright and dark regions in the whole image to a +x direction from a −x direction, compresses/processes the regions in the +x direction, and generates bright and dark region compressed images of all the rows,. In FIG. 24, as a result of the compression processing, the region detected as the bright region is indicated by an ON signal, and the region detected as the dark region is indicated by an OFF signal. Moreover, the image processor 20 detects the width (vertical width) of each of the ON and OFF signals indicating the compressed bright and dark regions in the y-axis direction.

The arrangement state of the probe array elements 3 in the array for biochemical examination sometimes has an inclination for each line. Therefore, when there is a difference in an inclination angle for each line as shown in FIG. 24, a difference is generated in the width of the y-axis direction among the respective ON signals, and a difference is generated in the width of the y-axis direction among the respective OFF signals.

The image processor 20 calculates the inclination angle (gradient) of the line of the probe array elements 3 in which the OFF signal having a largest width (compressed dark region) is generated, that is, the inclination angle of one line which contacts the region indicated by the OFF signal. Moreover, the image processor 20 regards the calculated inclination angles as the inclination angles (gradients) of all the line dividing lines.

Furthermore, the image processor 20 similarly detects the bright and dark regions in the whole image to a −y direction from a y direction, compresses/processes the regions in the −y direction, and generates the bright and dark region compressed images of all the lines. As a result of the compression processing, the region detected as the bright region is indicated by the ON signal, and the region detected as the dark region is indicated by the OFF signal. Moreover, the image processor 20 detects the width (lateral width) of each of the ON and OFF signals indicating the compressed bright and dark regions in the x-axis direction.

The arrangement state of the probe array elements 3 in the array for biochemical examination sometimes has an inclination for each row. Therefore, when there is a difference in the inclination angle for each row, a difference is generated in the width of the x-axis direction among the respective ON signals, and a difference is generated in the width of the x-axis direction among the respective OFF signals.

The image processor 20 calculates the inclination angle (gradient) of the row of the probe array elements 3 in which the OFF signal having a largest width (compressed dark region) is generated, that is, the inclination angle of one row which contacts the region indicated by the OFF signal. Moreover, the image processor 20 regards the calculated inclination angles as the inclination angles (gradients) of all the row dividing lines.

A first calculation example of an interval of the line dividing lines and an interval of the row dividing lines of the binarized sample fluorescent image will next be described. As shown in FIG. 24, the image processor 20 obtains the middle position of each bright region of the compressed images of all the rows as p, and the middle position of each dark region of the compressed images of all the rows as q. Moreover, the image processor 20 calculates the interval of the line dividing lines based on each point indicating the middle position p of each bright region. Alternatively, the image processor 20 calculates the interval of the line dividing lines based on each point indicating the middle position q of each dark region.

Moreover, the image processor 20 obtains the middle position of each bright region of the compressed images of all the lines as p' (not shown), and the middle position of each dark region of the compressed images of all the lines as q' (not shown). Furthermore, the image processor 20 calculates the interval of the row dividing lines based on each point indicating the middle position p' of each bright region. Alternatively, the image processor 20 calculates the interval of the row dividing lines based on each point indicating the middle position q' of each dark region.

When foreign particles or the like are present on the array for biochemical examination 6 during the calculation of the gradients of the line and row dividing lines, the width of the compressed bright region is larger than the width of the original bright region compressed image only by the probe array element 3. In this case, the image processor 20 compares the width of each continuous bright region with the arrangement conditions of the probe array elements 3, and judges whether the width of the bright region corresponds to the width of the original bright region compressed image. Moreover, when there is a portion not corresponding to the width of the original bright region compressed image in each bright region, the image processor 20 replaces the region of the portion with the dark region based on the arrangement conditions of the probe array elements 3. Thereafter, the image processor 20 calculates the interval of the line dividing lines or the row dividing lines. Thereby, the gradients of the appropriate line and row dividing lines from which the influences by the foreign particles are removed can be calculated.

A second calculation example of the intervals of the line and row dividing lines of the binarized sample fluorescent image will next be described. When the number of markers for position detection (the number of probes for position detection) is $N_P=1, 2, 3, 4$, the image processor 20 detects the center position of the predetermined array elements for position detection 2 disposed in the array for biochemical examination, and calculates an initial position of the line and row dividing lines based on the center position. Moreover, the image processor 20 calculates the intervals of the line and row dividing lines based on the initial position and the arrangement conditions of the probe array elements 3 based on the array elements for position detection 2.

A determination processing of the measurement region in the divided image will next be described.

Figure 25:
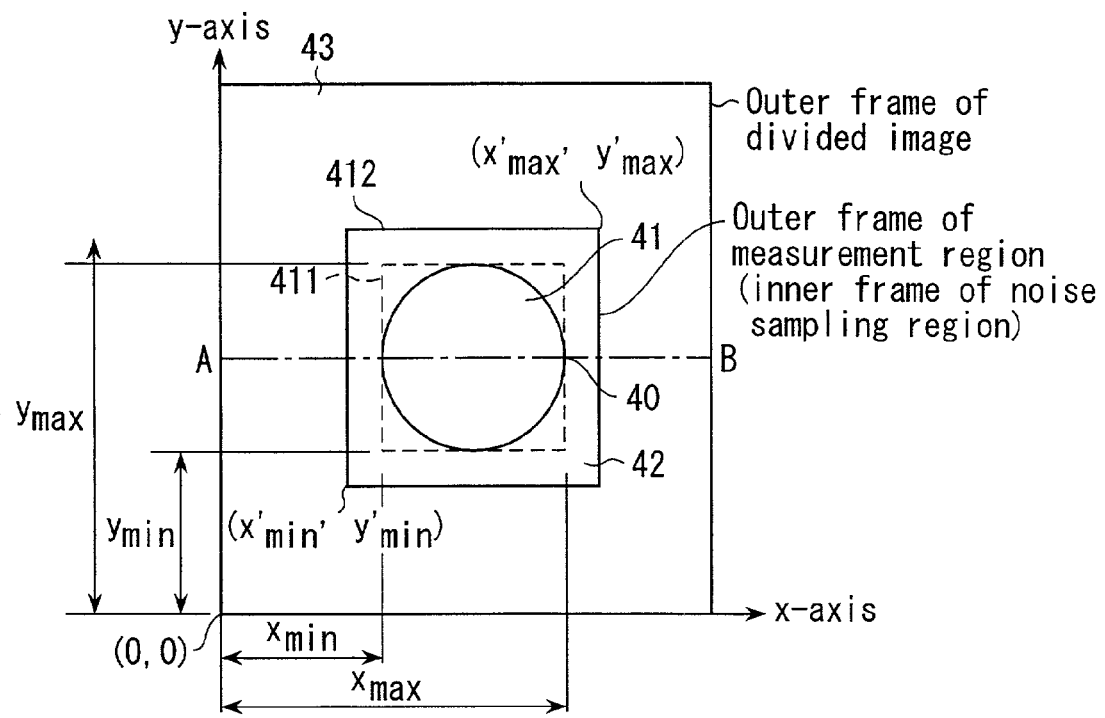
FIGS. 25, 26 are diagrams showing the divided images of the reference fluorescent image and sample fluorescent image according to the third embodiment of the present invention.

FIG. 25 is a diagram showing the divided images of the reference fluorescent image and sample fluorescent image. In FIG. 25, the same part as that of FIG. 4 is denoted with the same reference numerals. The image processor 20 binarizes the divided image with the middle value of output values in the divided image, and obtains the binarized image. Thereafter, the image processor 20 obtains a rectangle 412 constituted by expanding a rectangle 411 circumscribing a binarized line 40 of the binarized image by a constant amount as the boundary of the noise sampling region (local background region) 43. Moreover, the image processor 20 obtains the outside of the boundary as the noise sampling region 43 in the divided image, and the inside of the boundary as the measurement region 42. Thereby, the region including whole binarized region 41 and peripheries can be obtained as the measurement region 42.

Additionally, assuming that $\lambda$ is a fluorescent wavelength to be detected, a is a numerical aperture on the sample side, and $\Delta$ is a defocus amount, the image processor 20 determines an amount of expansion $\delta$ by the following equation.

$$\delta = 1.619 \times \lambda/a + a|\Delta|$$

Figure 26:
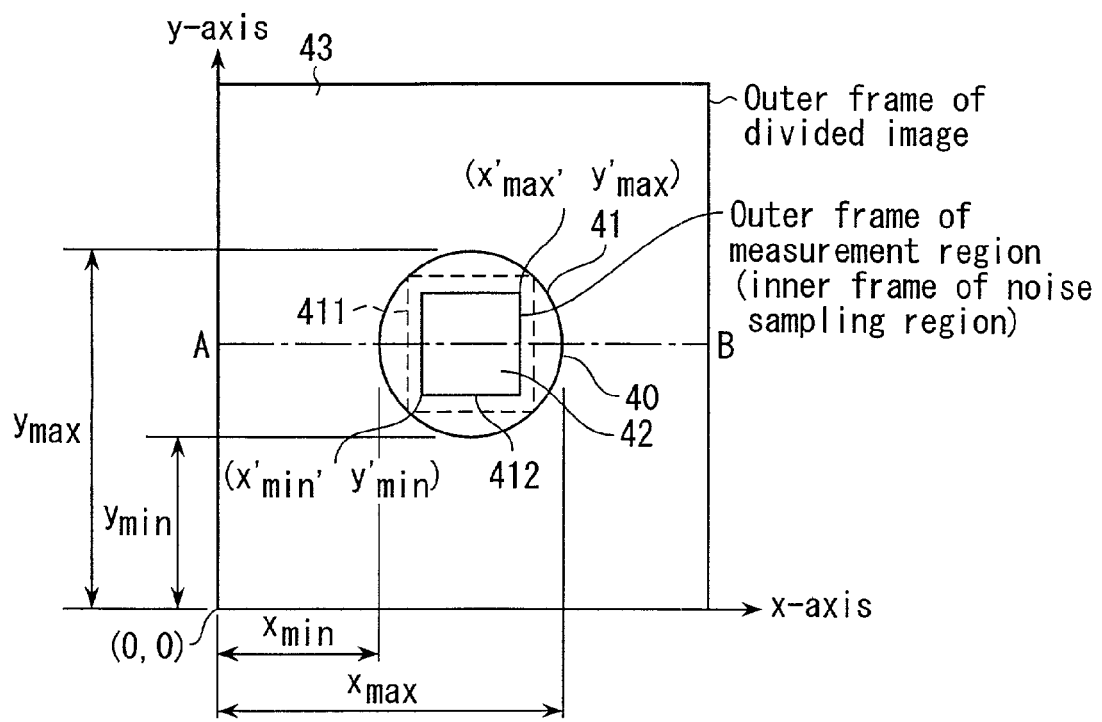

FIG. 26 is a diagram showing the divided images of the reference fluorescent image and sample fluorescent image. In FIG. 26, the same part as that of FIG. 4 is denoted with the same reference numerals. The image processor 20 binarizes the divided image with the middle value of the output values in the divided image, and obtains the binarized image. Thereafter, the image processor 20 obtains the rectangle 412 constituted by compressing the rectangle, 411 circumscribed by the binarized line 40 of the binarized image by the constant amount as the boundary of the measurement region 42. Moreover, the image processor 20 obtains the inside of the boundary as the measurement region 42 in the divided image, and the outside of the binarized line 40 as the noise sampling region 43. Thereby, only the binarized region 41 can be obtained as the measurement region 42.

Additionally, assuming that $\lambda$ is the fluorescent wavelength to be detected, a is the numerical aperture on the sample side, and $\Delta$ is the defocus amount, the image processor 20 can determine the amount of compression $\delta$ by the following equation.

$$\delta = 1.619 \times \lambda/a + a|\Delta|$$

After the determination processing of the measurement region shown in FIG. 25 or FIG. 26, the image processor 20 detects an intensity obtained by subtracting an average luminescent intensity per unit area of the noise sampling region 43 from the average luminescent intensity per unit area of the measurement region 42 as a reaction intensity of each probe.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biochemical examination method, comprising:

supplying a solution of a first biochemical material to an array for biochemical examination, which includes probe array elements arranged in columns and rows, in which respective second biochemical materials particularly reacting with the first biochemical material are held on a surface;

marking the first biochemical material with a luminescent molecule excitable by light so as to emit light to allow a luminescent intensity of the luminescent molecule for each of the probe array elements to be detected with an array detector, to enable a reaction state of the first biochemical material with the second biochemical materials particularly reacting with the first biochemical material to be examined for each of the probe array elements;

dividing a light image obtained by the array detector along column dividing lines and row dividing lines into a plurality of divided images corresponding to the probe array elements;

designating a measurement region and a local background region with respect to each of the divided images;

detecting a local background signal from the local background region;

using the detected local background signal to correct a detected signal from the measurement region;

wherein, when at least one of: (i) the columns have a plurality of respective different inclination angles, and (ii) the rows have a plurality of respective different inclination angles, an angle of inclination is determined for the corresponding at least one of the column dividing lines and the row dividing lines by:

binarizing the light image obtained by the array detector to obtain a binarized image;

compressing the binarized image along the at least one of the columns and the rows of the array to obtain compressed images of the at least one of the columns and the rows, said compressed images including bright regions corresponding to the one of the columns and the rows of the probe array elements and dark regions corresponding to regions between the one of the columns and the rows of the probe array elements;

detecting widths of the dark regions of the compressed images of the at least one of the columns and the rows, and identifying a broadest dark region having a broadest width among the dark regions of the compressed images of the corresponding one of the columns and the rows; and determining an angle of inclination of a column or a row corresponding to the broadest dark region, and setting said angle of inclination as an angle of inclination of a corresponding one of the column dividing lines and the row dividing lines; and wherein at least one of: (i) an interval between the column dividing lines, and (ii) an interval between the row dividing lines is determined by:

comparing the bright regions with arrangement conditions of the probe array elements;

replacing a part of a bright region that does not correspond to the arrangement conditions of the probe array elements with a dark region based on the arrangement conditions of the probe array elements; and determining the at least one of: (i) the interval between the column dividing lines and (ii) the interval between the row dividing lines, based on a plurality of points at respective middle positions of the dark regions and the bright regions of compressed images of the corresponding one of the array columns and the array rows.

2. The biochemical examination method according to claim 1, wherein the array for biochemical examination is configured by:

supplying a solution of a probe comprising the second biochemical materials into different positions of a surface of a reaction carrier having a solid structure formed of one of: (i) a porous material, a (ii) fibrous material and (iii) a molded material, holding the probe contained in the solution inside the one of: (i) the porous material, (ii) the fibrous material and (iii) the molded material, and supplying a solution of a sample to be examined containing the first biochemical material to the array for biochemical examination.

3. The biochemical examination method according to claim 1, wherein the solution of the first biochemical material comprises a mixture solution of a plurality of samples containing biochemical material labeled with a plurality of different luminescent molecules which are excitable by light; and wherein the method further comprises using a reference array in which the plurality of different luminescent molecules are mixed and held at a constant ratio, so that the reaction state of the second biochemical materials each of the probe array elements with the biochemical material in the mixture solution is examined.

4. The biochemical examination method according to claim 1, wherein the divided images are formed as parallelograms.

5. The biochemical examination method according to claim 1, further comprising setting a boundary of the measurement region as a boundary of the local background region.

6. The biochemical examination method according to claim 1, wherein the light image is binarized based on a median value of an output signal in an object region of the light image obtained by the array detector to obtain the binarized image.

7. The biochemical examination method according to claim 1, further comprising:

binarizing each the divided image with a median value of an output signal in the divided image;

defining an inner boundary of the local background region by expanding a rectangle circumscribing the binarized image by a constant amount; and defining an area outside of the boundary in the divided image as the local background region.

8. The biochemical examination method according to claim 1, further comprising:

binarizing each of the divided images based on a median value of an output signal in the divided images;

defining a boundary of the measurement region by compressing a rectangle circumscribed by the binarized image by a constant amount; and defining an area inside of the boundary as the measurement region.

9. The biochemical examination method according to claim 7, further comprising: determining an amount of expansion δ of the rectangle by the equation:

$$\delta = 1.619 \times \lambda/a + a|\Delta|$$

where:

λ is a fluorescent wavelength to be detected, a is a numerical aperture on a sample side of the array; and Δ is a defocus amount.

10. The biochemical examination method according to claim 8, further comprising determining the amount of compression δ of the rectangle by the equation:

$$\delta = 1.619 \times \lambda/a + a|\Delta|$$

where:
λ is a fluorescent wavelength to be detected,
a is a numerical aperture on a sample side of the array; and
Δ is a defocus amount.

11. The biochemical examination method according to claim 1, further comprising detecting a reaction intensity of each the probe array element by subtracting an average luminescent intensity per unit area of the local background region from an average luminescent intensity per unit area of the measurement region.

* * * * *